US005332573A

United States Patent [19]

[11] Patent Number: 5,332,573
[45] Date of Patent: Jul. 26, 1994

Yamaguchi et al.

[54] STRAINS OF DRECHSLERA SSP FOR CONTROLLING GRASS

[75] Inventors: Kenichi Yamaguchi, Mobara; Masanobu Arita, Kanagawa; Masatoshi Gohbara, Mobara; Tatsuo Shinmi, Mobara; Keiko Fukui, Mobara; Emi Tohyama, Mobara, all of Japan

[73] Assignee: Mitsui Toatsu Chemicals Inc., Tokyo, Japan

[21] Appl. No.: 76,689

[22] Filed: Jun. 15, 1993

Related U.S. Application Data

[63] Continuation of Ser. No. 764,675, Sep. 25, 1991, abandoned, which is a continuation-in-part of Ser. No. 711,529, Jun. 10, 1991, abandoned, and a continuation-in-part of Ser. No. 435,024, Nov. 13, 1989, abandoned.

[30] Foreign Application Priority Data

Nov. 21, 1988 [JP] Japan ................................ 63-292466
Jun. 13, 1990 [JP] Japan ................................ 2-152711

[51] Int. Cl.$^5$ ........................ A01N 63/00; C12N 1/00

[52] U.S. Cl. .................................... 504/117; 424/405; 435/254.1; 435/911; 504/101; 504/116

[58] Field of Search ............................ 435/254.1, 911; 424/93 R, 405; 504/101, 116, 117

[56] References Cited

U.S. PATENT DOCUMENTS 4,606,751 8/1986 Van Dyke et al. ..................... 71/79

FOREIGN PATENT DOCUMENTS 0207653 1/1987 European Pat. Off. .

OTHER PUBLICATIONS

Jong et al., PhD, ATCC of Fungi/Yeasts, 1987, 17th ed., p. 144.

Bio. Abst., Prete, 1984, (pp. 260-267); #80561 ref. #; Seed-borne fungi of weeds.

Robeson et al., Monocerin, a phytotoxin from *Exserohilium turcicum* (*Dreshtera turcica*), 1982, 2681-2682, etc.

Strubel, et al., The Incredible Fungal genus—Drechslera—and its Phytotoxic Ophiobolins, 1988, 145-151.

*Primary Examiner*—Douglas W. Robinson
*Assistant Examiner*—Deborah K. Ware
*Attorney, Agent, or Firm*—Nixon & Vanderhye

[57] ABSTRACT

Described are new strains of Drechslera spp., which possess herbicidal effects against all varieties of barnyard grass, i.e., Echinochloa spp. but do not give any influence to crops under cultivation such as rice. The control agents according to the present invention, which contain one or more of the strains, have high safety and selectivity, thereby providing practical control effects against barnyard grass. Further, the control compositions according to the present invention, which contain one or more of the new strains in combination with one or more chemical herbicides, have sufficient herbicidal effects even at dosages which are too low to permit control of barnyard grass when they are applied singly, thereby making it possible to reduce the dosage of herbicides. Thus, the control compositions can therefore contribute to the prevention of environmental pollution and the occurrence of barnyard grass with acquired pesticide resistance.

4 Claims, No Drawings

STRAINS OF DRECHSLERA SSP FOR CONTROLLING GRASS

This is a continuation of application Ser. No. 07/764,675, filed Sep. 25, 1991, and a continuation-in-part of 07/435,024 filed Nov. 13, 1989, which is a continuation-in-part of 07/711,529, filed Jun. 10, 1991, all now abandoned.

BACKGROUND OF THE INVENTION

1) Field of the Invention

The present invention relates to weed control compositions comprising living fungal cells or metabolites of plant pathogens effective for the control of weeds, especially, barnyard grass (Echinochloa) which is a troublesome weed in the cultivation of economic crops, for example, important crops of Gramineae such as rice and wheat, and also to methods for controlling weeds by using metabolites of such fungi.

2) Description of the Related Art

Regarding control methods of weeds, plant diseases and insects, substantial development has taken place approximately in last 100 years owing to developments in chemistry. As a result, chemical control methods have replaced traditional cultivation control methods. In particular, the rapidly progress of synthesized organic pesticides in the middle Nineteen Hundreds, typified by DDT, led to increased field crop yields, improved quality, farming labor saving, etc., so that the world food production was improved rapidly. Serious problems have, however, arisen in last several years from the use of such synthesized organic pesticides, including environmental pollution and reduced control effects resulted from the occurrence of pathogens and insect pests with acquired pesticides resistance. In recent years, the development of synthetic pesticides is therefore apparently oriented toward higher activity of pesticides. Namely, pesticides are developed these days which are harmless to mammals and produce good effects at low application rates while paying sufficient attention to residuality, environmental pollution and the like. On the other hand, there is recently a growing interest in so-called organic agriculture system in which crops are cultivated without pesticides. People are very concerned with the influence of synthetic organic pesticides to the human body and their influence to the natural environment as mentioned above and in recent years, the interests in biopesticides has increased enormously so a great deal of research and development work is under way with respect to biopesticides. The establishment of a total control system relying upon the combination of a biological control method, which makes use of a natural enemy or the like, and a cultivation or cultural control method involving the use of a cultivation system, such as crop rotation, may be mentioned by way of example.

From the foregoing background, there is a keen demand for the establishment of biological control methods. A great hope is placed especially on the development of biopesticides directly using the living cells of a microorganism and microbial origin pesticides using a physiologically active substance produced by a microorganism. In the field of herbicides, extensive investigations are carried out in recent years on mycoherbicides which use a pathogen against weeds. Mycoherbicides which have already been put on the market include "DeVine" (trade mark; product of Abbott Laboratories Ltd.) and "Coilego" (trade mark; product of Ecogen Ltd.). These two mycoherbicides are employed for the control of strangle vine and northern jointvetch, respectively. In addition, a mycoherbicide effective for the control of sicklepod in peanut and soybean fields is said to be commercially available soon from Mycogen Ltd. Neither mycoherbicide nor microbial origin herbicides are yet available against barnyard grass (Echinochloa spp.) which is a troublesome weed in the cultivation of important crops such as rice and wheat.

SUMMARY OF THE INVENTION

An object of this invention is to solve the above-described current deficiencies in the production of the crops and hence to provide novel weed control means capable of taking over the position of synthesized herbicides.

The present inventors have found certain new strains of the fungus Drechslera spp. as pathogens effective for the control of barnyard grass (Echinochloa spp.) which is a troublesome weed in the cultivation of economic crops such as rice and wheat.

The present invention therefore provides a weed control composition comprising living Drechslera spp. fungal cells or a metabolite thereof as well as a weed control method using living fungal cells or a metabolite of Drechslera spp.

The pathogens, Drechslera spp., useful in the practice of this invention exhibit a specific pathogenecity to barnyard grass. The use of these microorganisms as mycoherbicide makes it possible to control barnyard grass, a troublesome weed, without adversely affecting adjacent economic crops.

Further, the pathogens which are useful in the practice of this invention have been chosen from a variety naturally occurring of microorganisms and therefore, are free of the potential problem of environmental pollution by synthesized organic herbicides and can be used safely.

The present invention also provides a weed-control composition comprising a strain of Drechslera spp., a chemical herbicide and an agriculturally acceptable carrier, said strain of Drechslera spp. being free of pathogenecity against economic crops but having pathogenecity against Echinochloa spp.

The present invention can therefore reduce the dosage of a chemical herbicide while ensuring safer and sufficient control of weeds.

DETAILED DESCRIPTION OF THE INVENTION

With a view toward controlling barnyard grass which is a troublesome weed in both upland and paddy fields, the present inventors were interested in pathogens against barnyard grass and therefore investigated numerous microorganisms of this type. As a result, many of mold fungi drechslera spp. are pathogens which possess herbicidal activities against barnyard grass but have no pathogenecity against crops such as rice and wheat, leading to the completion of this invention.

Barnyard grass, which is the target weed of the present invention, is a weed belonging to the genus Echinochloa. which in turn falls under the order of Graminales . Described specifically, it includes the following varieties: *Echinochloa oryzicola, Echinochloa crus*-galli vat. formosensis, *Echinochloa crus*-galli vat. crus-galli, *Echinochloa crus*-galli vat. praticola. *Echinochloa colo-*

*num, Echinochloa pyramidalis, Echinochloa stagnina* and *Echinochloa haploclada.*

The microorganisms according to the present invention are new strains of Drechslera spp., which possess no pathogenecity against cultivated crops—such as rice, barley, wheat, rye, wild oat, corn, sorghum and foxtail millet—and pastures—such as orchard grass, Italian rye grass, perennial rye grass, sweet barnal grass, tall fescue, and meadow fescue—but have pathogenecity against *Echinochloa oryzicola, Echinochloa crus*-galli, *Echinochloa colonum* and the like.

Namely, Drechslera spp. useful in the practice of this invention were found by subjecting to pure isolation pathogens, which had been collected from lesions of naturally-infected barnyard grass, and then selecting, from the thus-isolated pathogens, those having pathogenecity against barnyard grass but being free of pathogenecity against economic crops typified by rice.

Pathogens useful in the practice of this invention were selected by conducting both herbicidal activity and parasiticity tests on barnyard grass and rice plants with respect to strains isolated from naturally-infected barnyard grass. As a result of a morphological identification of obtained six strains with the activity of the controlling barnyard grass, they were found to be classified as *Drechslera monoceras* (9 strains; MH-0015, MH-2653, MH-2679, MH-4418, MH-5011, MH-5017, MH-5018, MH-5511 or MH-9011), *Drechslera ravenelli* (2 strains; MH-0042, MH-0060) and *Drechslera poa* (1 strain; MH-0122).

The weed control compositions of this invention, which possess the specific pathogenecity against barnyard grass only, can use any one of the above-selected strains of Drechslera spp.

As a method for using Drechslera spp. in such weed control compositions, cultured living fungal cells can be used directly as they are or after culturing the cells, the culture resulting from germ-free filtration to use a metabolite thereof.

According to the former method, a weed control composition can be obtained by suspending spores, which have been obtained by culturing Drechslera spp. on a nutrient medium, in an aqueous solution of a non-ionic surfactant such as "Trifon X-100" (trade name) or "Tween 80" (trade name).

Spores of Drechslera spp. can be obtained whether the nutrient medium is in a liquid form or in a solid form. When a liquid culture medium is desired, a potato-dextrose liquid culture medium or an oatmeal liquid culture medium is inoculated with cells. The cells are allowed to grow there. Resultant cells are collected. Mycelia of Drechslera spp. thus obtained are ground, spread on a filter paper and then left to grow and form spores. When a solid culture medium is desired on the other hand, cells are cultured on a potatodextrose agar medium or oatmeal agar medium. Aerial hyphae are then removed with distilled water, whereby spores of Drechslera spp. can be obtained.

On the other hand, according to the latter method in which a cell metabolite is used, Drechslera spp. are subjected to static culture on a potato-dextrose liquid culture medium. The resulting culture is subjected to germ-free filtration and the filtrate containing the cellular metabolites is formulated into a weed control composition.

Effective microbial weed control compositions and microbial origin weed control compositions can be produced by mass-culturing Drechslera spp. and efficiently obtaining spores, both under asceptic conditions. When applied to the field, i.e., paddy fields before and after transplantation of rice seedlings, these weed control compositions possess selective herbicidal activities against barnyard grass only and show substantially to pathogenecity against economic crops such as rice, wheat, barley and corn. They therefore have highly-selective herbicidal activities, and are free of potential problem of environmental contamination and thus can be used safely.

The microorganisms of the present invention can be used as weed control agents in various ways. Living fungal cells obtained by culture of each microorganism can be used directly, i.e., as they are. It is also possible to use a filtrate obtained subsequent to culture of cells. As a further alternative, it is also possible to use both the living fungal cells and the liltrate as a mixture. In addition, each microorganism of the present invention can also be used either singly by suspending its conidia and hyphae, which have been obtained by culturing the microorganism on a nutrient medium, in an aqueous solution containing a surfactant or the like or in combination with one or more chemical pesticides such as other herbicides which do not exhibit competition with the microorganism, fungicides and insecticides. When the microorganisms according to the present invention are used as weed control agents, conidia having higher durability than hyphae are more desired. Although proliferation of cells of each microorganism according to the present invention is feasible whether a liquid medium or a solid medium is used, conidia can be formed by inoculating cells to a liquid medium such as a potato-dextrose medium, allowing the cells to proliferate, disrupting cells so obtained, and then drying the cells so disrupted. In the case of a solid medium, formation of conidia can be promoted by inoculating cells to a potato-dextrose-agar medium or the like, removing grown aerial hyphae and then drying cells so obtained.

The microorganisms according to the-present invention permit mass production of cells such as conidia and/or hyphae as described above, so that they can be used industrially as weed control agents. Further, these weed control agents - when applied, for example, at the time of transplanting of rice seedlings to a paddy field - exhibit herbicidal effects against barnyard grass as a weed and have pathogenecity against neither cultivated crops such as rice, barley, wheat, rye, wild oat, corn, sorghum and foxtail millet nor pastures such as orchard grass, Italian rye grass, perennial rye grass, sweet barnal grass, tall fescue, meadow rescue and meadow fescue. The weed control agents therefore can provide selective herbicidal effects.

The Drechslera strains according to the present invention are absolutely free from biological effects of certain chemical herbicides, such as inhibition to hyphal growth and inhibition to spore germination. Their combined use can bring about substantial improvements in the herbicidal effects against barnyard grass.

Further, weed control compositions which comprise in combination at least one of the Drechslera fungi according to the present invention, i.e., *Drechslera monoceras, Drechslera ravenelii* and/or *Drechslera poae* and at least one conventional chemical herbicide-make it possible to control barnyard grass at such low dosages that the conventional chemical herbicide cannot control it. Examples of the conventional chemical herbicide include oxadiazon, dimethametryne, simetryne, chlormethoxynil, dimepiperate, trifluralin, naproanilide, paraquat, pyrazoxyfen, pyrazolate, butachlor, pretilachlor, benthiocarb, mefenacet, molinate, CNP, DBN, MCP, prometryne, benzofenap, propanil, NSK-850, HW-52, clomeprop, esprocarb, bifenox, quinchlorac, buromobutide, bensulfuron methyl, pyrazosulfuron ethyl, and 2,4-D.

Regarding the mechanism of action by each weed control composition according to the present invention, it appears that absorption and transfer of the chemical herbicide may be promoted through invasive scars formed in plant tissues as a result of infection from the Drechslera strain and infection from the Drechslera strain may also be facilitated in plant tissues damaged by the chemical herbicide. The reduced dosage of the chemical herbicide owing to such synergistic action of the Drechslera strain and the chemical herbicides can improve today's various problems such as environmental pollution and the occurrence of resistant weeds and can substantially benefit not only agricultural producers but also general consumers.

The new strains of Drechslera spp., which pertain to the present invention, have been found to have pathogenecity against all the species of Echinochloa spp., i.e., barnyard grass as a weed and have shown practical herbicidal effects against barnyard grass. They have also been confirmed to be extremely safe for cultivated crops led by rice.

The microorganisms according to the present invention have been selected from microorganisms in the nature, so that they are free of the potential problem of environmental pollution by synthetic organic pesticides and are therefore safe.

The weed control compositions according to the present invention, each of which contains a Drechslera strain and a chemical herbicide in combination, can show sufficient herbicidal effects at dosages which are too small to control weeds when they are used singly. They have therefore made it possible to lower the dosage of chemical herbicides. The synergistic action of the Drechslera strains and the chemical herbicides have also made it possible to reduce the amount of conidia of the Drechslera strain to be applied, resulting in a reduction in the production cost.

The weed control agents and weed control compositions according to the present invention therefore contribute not only to the production of crops but also to the prevention of the today's problems, namely, environmental pollution and the occurrence of weeds with acquired pesticide resistance.

To use as herbicides the weed control agents and weed control compositions according to the present invention, cells of the Drechslera strain may be used as they are, together with the chemical herbicide in an undiluted form. It is however generally desirable to mix cells of the Drechslera strain and the undiluted chemical herbicide with an inert solid or liquid carrier and then to prepare the resultant mixture into a formulation form commonly employed in the art, such as a granular formulation, a flowable formulation, a wettable powder, an emulsion or a liquid formulation.

Any carriers can be used whether they are solid or liquid, as long as they are usually employed in agricultural and horticultural pesticides and are biologically inert. They should not be limited to any particular ones.

Examples of solid carriers include mineral powders such as clay, talc, bentonite, calcium carbonate, diatomaceous earth and white carbon; vegetable flours such as soybean flour and starch; and high molecular compounds such as polyvinyl alcohol and polyalkylene glycol. On the other hand, exemplary liquid carries include various organic solvents such as decane and dodecane; vegetable oils; mineral oils; and water.

The content of the Drechslera strain in each weed control agent according to the present invention can, in terms of spores, be $10^2$–$10^{12}$ spores, preferably $10^6$–$10^{12}$ spores per kilogram.

The content of the chemical herbicide in each weed control composition according to the present invention varies depending on the formulation form. In general, it can be 0.05–15 wt.% in a granular formulation, 1–50 wt.% in a flowable formulation, and 1–90 wt.% in a wettable powder. Its preferred content is 0.5–8 wt.% in a granular formulation, 10–30 wt.% in a flowable formulation, and 10–50 wt.% in a wettable powder. On the other hand, the content of the Drechslera strain can, in terms of spores, $10^2$–$10^{12}$ spores, preferably $10^6$–$10^{12}$ per kilogram of the effective ingredients in the composition.

As adjuvants, surfactants, binders, stabilizers and the like, which are commonly used in agricultural and horticultural pesticides, can be used either singly or in combination as needed. As stabilizers, an antioxidant and/or a pH regulator may be used by way of example, A light stabilizer may also be used in some instances.

The total content of such adjuvants may range from 0 wt.% to 80 wt.%. The content of the carrier is therefore the value which is obtained by subtracting the contents of the effective ingredients and adjuvants from 100 wt.%.

When the weed control agents and weed control compositions according to the present invention are applied to a field, their dosage can, in terms of the amount of conidia of the Drechslera strain, be $10^2$–$10^{15}$ spores per 10 a, preferably $10^7$–$10^{12}$ spores per 10 a.

The weed control compositions according to the present invention contain one or more species of Drechslera spp. in combination with one or more of chemical herbicides. These weed control compositions can be used in the form of mixtures with pesticides such as fungicides having no antifungal activities against Drechslera spp., insecticides and plant growth regulators, fertilizers, soil improvers and the like, to say nothing of their combined application.

Examples of usable chemical herbicides include: 2,4-dichloro-o-methylphenoxyacetic acid (2,4-D), 4-chlorophenoxyacetic acid (MCPA), 2,4,5-trichlorophenoxyacetic acid (2,4,5-T), 2-(2,4-dichlorophenoxy)propionic acid (dichlorprop), 2-(2-methyl-4-chlorophenoxy)propionic acid (mecoprop), 2-(2,4,5-trichlorophenoxy)propionic acid (fenoprop), 4-(2,4-dichlorophenoxy)butyric acid (2,4-DB), 4-(2-methyl-4-chlorophenoxy)butyric acid (MCPB), 2-(2-naphthoxy)propionanilide (naproanilide), 2-(1-naphthoxy)N,N-diethylpropionamide (napropamid), methyl ($\pm$)-2-[4-(2,4-dichlorophenoxy)-phenoxy]propionate (diclofop-methyl), butyl 2-[4-(5-trifluoromethyl-2-pyridyloxy)phenoxy]propionate (fluazifop), methyl 2-[4-(3-chloro-5-trifluoromethyl-fluoromethyl-2-pyridyloxy)phenoxy]propionate (haloxyfop), 2-propynyl 2-[4-(3,5-dichloro-2-pyridyloxy)-phenoxy]propionate (chlorazifop-propynyl), ethyl 2-[4-(6-chloro-2-quinoxalinyloxy)phenoxy]propionate (quizalofop-ethyl), ethyl 2-[4-(6-chloro-2-benzoxazolyl)phenoxy]propionate (fenoxaprop-ethyl), ethyl 2-[4-(6-chloro-2-benzothiazolyloxy)phenoxy]propionate (fenthiaprop-ethyl), 2,3,6-trichlorobenzoic acid (2,3,6-TBA), 3,6-dichloro-2-methoxybenzoic acid (dicamba), 2,5-dichloro-3-aminobenzoic acid (amiben), 3,5,6-trichloro-2-methoxybenzoic acid (tricamba), 4-chloro-2,2-dimethylvaleranilide (monalide), 3,4-dichloropropionanilide (propanil), 3,4-dichloro-2-methylacrylanilide (dicryl), 3,4-dichlorocyclopropanecarboxanilide (cypromid), 3,4-dichloro-2-methylpentananilide (karsil), 3-chloro-2,4-dimethylpentananilide (solan), N-(1,1-dimethylpropynyl)-3,5-dichlorobenzamide (propyzamide), N,N-dimethyl-2,2-diphenylacetamide (diphenamide), N-naphthylphthalamic acid (naptalam), N-(1,1-dimethylbenzyl)-2-bromo-3,3-dimethylbutanamide (buromobutide), 2-benzothiazol-2-yl-oxy-N-methylacetanilide (mefenacet), N-[3-(1-ethyl-1-methylpropyl)5-isoxazolyl]-2,6-dimethoxybenzamide (isoxaben), 1,1-dimethyl-3-phenylurea (fenuron), 3-(4-chlorophenyl)-1,1-dimethylurea (monuron), 3-(4-chlorophenyl)-2,1,1-trimethylisourea (trimeturon), 3-(4-chlorophenyl)-1-methoxy-1-methylurea (monolinuron), 3-(4-chlorophenyl)-1-methyl-1-(1-methylpropyn-2-yl)urea (buturon), 3-(4-bromophenyl)-1-methoxy-1-methylurea (metobromuron), 1-(2-methylcyclohexyl)-3-phenylurea (siduron), 1,1-dimethyl-3-(3-trifluoromethylphenyl)urea (fluometuron), 3-(3,4-dichlorophenyl)-1,1-dimethylurea (diuron), 3-(3,4-dichlorophenyl)-1-methoxy-1-methylurea (linuron), 3-(3,4-dichlorophenyl)-1-n-butyl-1-methylurea (neburon), 3-(3-chloro-4-methoxyphenyl)-1,1-dimethylurea (metoxuron), 3-(4-bromo-3-chlorophenyl)-1-methoxy-1-methylurea (chlorbromuron), 3-(4-difluorochloromethylthio-3-chlorophenyl)-1,1-dimethylurea (fluothiuron), 3-(3-chloro-4-methylphenyl)-1,1-dimethylurea (chlortoluron), 3-[4-(4-chlorophenoxy)-phenyl]-1,1-dimethylurea (chloroxuron), 3-[4-(4-methoxyphenoxy)phenyl]-1,1-dimethylurea (difenoxuron), 3-[3-(N-tertiary-butylcarbamoyloxy)phenyl]-1,1-dimethylurea (karbutilate), 3-benzoyl-3-(3,4-dichlorophenyl)-1,1-dimethylurea (phenobenzuron), 1-α,α-dimethylbenzyl)-3-(4-methylphenyl)urea (dymron), 3-(4-isopropylphenyl)-1,1-dimethylurea (isoproturon), 3-(2-benzothiazolyl)-1,3-dimethylurea (methabenzthiazuron), 3-(2-benzothiazolyl)-1-methylurea (benzthiazuron), 3-(hexahydro-4,7-methanoindan-5-yl)-1,1-dimethylurea (noruron), 3-cyclooctyl-1,1-dimethylurea (cycluron), 1,3-dimethyl-3-(5-trifluoromethyl-1,3,4-thiadiazol-2-yl)urea (thiazfluron), 1-(5-ethylsulfonyl-1,3,4-thiadiazol-2-yl)-1,3-dimethylurea (sulfodiazol), 3-[5-(1,1-dimethylethyl)-1,3,4-thiadiazol-2-yl]-1,3-dimethylurea (tebuthiuron), 3-(5-tertiary-butylisoxazol-3-yl)-1,1-dimethylurea (isouron), 4-[2-chloro-4-(3,3-dimethylureido)phenyl]-2-tertiary-butyl-1,3,4-oxadiazolin-5-one (dimefuron), 3-(5-tertiarybutyl-1,3,4-thiadiazol-2-yl)-4-hydroxy-1-methyl-2-imidazolidinone (buthidazole), 2-chloro-4,6-bis(ethylamino)-1,3,5-triazine (simazine), 2-chloro-4-ethylamino-6-isopropylamino-1,3,5-triazine (atrazine), 2-chloro-4,6-bis(isopropylamino)-1,3,5-triazine (propazine), 2-chloro-4-diethylamino-6-ethylamino-1,3,5-triazine (trietazine), 2-chloro-4-ethylamino-6-tertiary-butylamino-1,3,5-triazine (terbuthylazine), 2-(4-chloro-6-ethylamino-1,3,5-triazin-2-yl-amino)2-methylpropionitrile (cyanazine), 2-chloro-4-cyclopropylamino-6-isopropylamino-1,3,5-triazine (prefox), 2-[4-chloro-4-(cyclopropylamino)-1,3,5-triazin-2-yl-amino]-2-methylpropionitrile (procyazin), 6-methoxy-2-secondary-butylamino-4-ethylamino-1,3,5-triazine (secbumeton), 6-methoxy-2,4-bis(isopropylamino)-1,3,5-triazine (prometone), 6-methylthio-2,4-bis(ethylamino)-1,3,5-triazine (simetryne), 6-methylthio-2,4-bis(isopropylamino)-1,3,5-triazine (prometryne), 6-methylthio-2-methylamino-4-isopropylamino-1,3,5-triazine (ametryne), 6-methylthio-2-ethylamino-4-tertiarybutylamino-1,3,5-triazine (terbutryn), 6-methylthio-2-isopropylamino-4-(3-methoxypropylamino)-1,3,5-triazine (methoprotryne), 6-methylthio-2-(1,2-dimethylpropylamino)-4-ethylamino-1,3,5-triazine (dimethametryne), 6-methylthio-2-isopropylamino-4-methylamino-1,3,5-triazine (desmetryne), 4-amino-6-tertiary-butyl-3-methylthio-1,2,4-triazin-5(4H)-one (metribuzin), 2-ethylthio-4,6-bis(isopropylamino)-1,3,5-triazine (dipropetryn), 2-tertiary-butylamino-4-ethylamino-6-methoxyamino-1,3,5-triazine (terbumeton), 2-azide-4-isopropylamino-6-methylthio-1,3,5-triazine (aziprotryne), 4-amino-3-methyl-6-phenyl-1,2,4-triazin-5(4H)-one (metamitron), 6-tertiary-butyl-4-isobutylideneamino-1,2,4-triazin-5(4H)-one (isomethiozin), 3-cyclohexyl-6-dimethylamino-1-methyl-1,3,5-triazin-2,4-(1H,3H)-dione (hexazinone), ethyl-N-(4-chloro-6-ethylamino-1,3,5-triazin-2-yl)-aminoacetate (eglinazine), ethyl-N-(4-chloro-6-isopropylamino-1,3,5-triazin-2-yl)-aminoacetate (proglinazine), 2-chloro-N-isopropylacetanilide (propachlor), N-methoxymethyl-2',6'-diethyl-2-chloroacetanilide (alachlor), 2-chloro-2',6'-diethyl-N-(buthoxymethyl)acetanilide (butachlor), 2-chloro-2'-ethyl-6'-methyl-N-(2-methoxy-1-methylethyl)acetanilide (metolachlor), N,N-diaryl-2-chloroacetamide (allidochlor), 2-chloro-2',6'-dimethyl-N-(2-methoxyethyl)acetanilide (dimethachlor), 2,6-dinitro-N,N-dipropyl-4-trifluoromethylaniline (trifluralin), N-butyl-N-ethyl-2,6-dinitro-4-trifluoromethylaniline (benfluralin), 2,6-dinitro-N-propyl-N-cyclopropyl-4-trifluoromethylaniline (profluralin), N,N-diethyl-2,4-dinitro-6-trifluoromethyl-m-phenylenediamine (dinitramin), 4-isopropyl-2,6-dinitro-N,N-dipropylaniline (isopropaline), 2,6-dinitro-N-secondary-butyl-4-tertiary-butylaniline (buttalin), 4-methylsulfonyl-2,6-dinitro-N,N-dipropylaniline (nittalin), 3,4-dimethyl-2,6-dinitro-N-1-ethylpropylaniline (pendimethalin), 3,5-dinitro-4-dipropylaminobenzensulfonamide (oryzalin), N-ethyl-N-(2-methylallyl-2,6-dinitro-4-(trifluoromethyl)aniline (ethalflutalin), N,N-diethyl-2,4-dinitro-6-trifluoromethyl-m-phenylenediamine (diethamine), 2-chloro-N-(4-methoxy-6-methyl-1,3,5-triazin-2-yl-aminocarbonyl)-benzenesulfonamide (chlorsulfuron), methyl 2-[3-(4-methoxy-6-methyl-1,3,5-triazin-2-yl)ureidosulfonyl]-benzoate (metsulfuron-methyl), methyl 2-[3-(4,6-dimethoxypyrimidin-2-yl)ureidosulfonylmethyl]benzoate (bensulfuron), ethyl 2-[3-(4-chloro-6-methoxypyrimidin-2-yl)ureidosulfonyl]benzoate (chlorinuronethyl), methyl 3-[3-(4-methoxy-6-methyl-1,3,5-triazin-2-yl)ureidosulfonyl]-thiophenecarboxylic acid (thiameturon), Ethyl 5-[3-(4,6-dimethoxypyrimidin-2-yl)ureidosulfonyl]-1-methylpyrazole-4-carboxylate (pyrazosulfuron ethyl), 3-(4,6-dimethoxy-1,3,5-triazin-2-yl)-1-[2-(2-methoxyethoxy)-phenylsulfonyl]urea (esnosufuron), 3,7-2dichloro-8-quinolinecarboxylic acid (quinchlorac), 3,6-dichloro-2-pyridinecarboxylic acid (clopyralid), α-(2-chlorophenyl)-α-(4-chlorophenyl)-5-pyrimidinemethanol (fenarimol), S,S-dimethyl-2-(difluoromethyl)-4-(2-methylpropyl)-6-trifluoromethyl-3,5-pyridinedicarbothioate (dithiopyr), 4-chloro-5-(methylamino)-2-(3-trifluoromethylphenyl)-3(2H)-pyridazinone (norflurazon), O,O-bis(1'-methylethyl)-S-[2-(phenylsulfonyl)aminoethyl]phosphorodithioate (bensulide), (+)-2-[4,5-dihydro-4-methyl-4-(1-methylethyl)-5-oxo-1H-imidazole-2-yl]-5-ethyl-3-pyridinecarboxylic acid (imazaethapyr), 3-[5-(1,1-dimethylethyl)-3-isoxazolyl]-4-hydroxy-1-methyl-2-imidazolidione (busoxinone), 2-[1-(ethoxyimino)butyl]-3-hydroxy-5-(2H-tetrahydrothiopyran-3-yl)-2-cyclohexene-1-one (cycloxydim), S-(4-chlorobenzyl)N,N-diethylthiocarbamate (benthiocarb), S-etnyl N,N-hexamethylenethiocarbamate (molinate), isopropyl-N-phenylcarbamate (propham), isopropyl N-(3-chlorophenyl)carbamate (chloro propham), methyl N-(3,4-dichlorophenyl)carbamate (swep), 3-(ethoxycarbonylamino)phenyl N-phenylcarbamate (desmedipham), 3-(methoxycarbonylamino)phenyl N-(3-methylphenyl)carbamate (phenmedipham), S-2,3-dichloro-2-propenyl N,N-diisopropylthicarbamate (diallate), S-ethyl N,N-di-n-propylthiocarbamate (EPTC), S-ethyl N-cyclohexyl-N-ethyltiocarbamate (cycloate), methyl N-(4-aminobenzenesulfony)carbamate (asulam), S-$\alpha,\alpha$-dimethylbenzyl)piperidine-1-carbothioate (dimepiperate), S-benzyl N-ethyl-N-(1,2-dimethylpropyl)thiocarbamate (esprocarb), O-(3-tertbuthylphenyl) N-(6-methoxy-2-pyridyl)-N-methyl thiocarbamate (pributycarb), 2,4-dichlorophenyl-3-methoxy-4-nitrophenylether (chlomethoxynil), 2,4,6-trichlorophenyl-4-nitrophenylether (CNP), methyl-5-(2,4-dichlorophenoxy)-2-nitrobenzoate (bifenox), sodium 5-(2-chloro-4-trifluoromethylphenoxy)-2-nitrobenzoate (acifluorfensodium), 1-ethoxycarbonylethyl-5-(2-chloro-4-trifluoromethylphenoxy)-2-nitrobenzoate (lactofen), 5-(2-chloro-4-trifluoromethylphenoxy)-N-methanesulufonyl-2-nitrobenzamido (fomesafen), 2-chloro-2',6'-diethyl-N-(n-propoxyethyl)-acetanilide (pretilachlor), 2-(2,4-dichloro-3-methylphenoxy)propionanilide (clomeprop), 5-tert-butyl-3-(2,4-dichloro-5-isopropoxyphenyl)-1,3,4-oxadiazol-2(3H)-one (oxadiazon), 2-(3',4'-dichlorophenyl)-4-methyl-1,2,4-oxadiazolidine-3,5-dione (methazole), 3-isopropyl-1H-2,1,3-benzothiadiazin-4-(3H)one-2,2-dioxide (bentazone), 4-(2,4-dichlorobenzoyl)-1,3-dimethyl-1H-pyrazol-5-yl-p-toluenesulfonate (pyrazolate), 4-(2,4-dichlorobenzyl)-1,3-dimethyl-5-phenacyloxy-1H-pyrazole (pyrazoxyfen), 4-(2,4-dichloro-3-methylbenzyl)-1-,3-dimethyl-5-(4-methylphenacyloxy)-1 H-pyrazole benzofenap), 2-(4-isopropyl-4-methyl-5-oxo-imidazolin-2-yl)-3-quinolinic acid (imazaquin), and 2-chloro-N-(3-methoxy-2-thienyl)methyl-2',6'-dimethylacetanilide (NSK-850).

In particular, when weed control compositions according to the present invention contain one or more of herbicides for barnyard grass, for example, one or more of chemical herbicides such as diphenyl ether herbicides, anilide herbicides and thiolcarbamate herbicides, synergistic herbicidal effects which are so large that cannot be expected when they are applied individually can be obtained, thereby making it possible to control barnyard grass at an unexpectedly low dosage.

Further, when weed control compositions according to the present invention contain one or more of herbicides for broad-leaf weeds, for example, one or more of chemical herbicides such as sulfonylurea herbicides and triazine herbicides, synergistic herbicidal effects which are so large that cannot be expected when they are applied individually can be obtained. It is therefore possible to reduce the dosage of the pathogen, one of the two effective ingredients, and also to lower the dosage of the chemical herbicide. In addition, various lowland weeds can be controlled owing to the broad-spectrum herbicidal effects of the compositions.

Pathogens Drechslera spp. useful in the practice of this invention will hereinafter be specifically described by the following examples. It should however be borne in mind that the present invention is not limited thereto.

EXAMPLE 1

Isolation and Identification of Effective Pathogen

1) Isolation method of pathogen:

Naturally-infected barnyard grass was collected from a paddy field. Centering at individual lesions, leaf pieces of 10–20 mm long were cut off. The pieces of barnyard grass dipped for 1–2 seconds in a 70% ethyl alcohol solution and then for 10 minutes in sodium hypochlorite solution having an effective chlorine concentration of 2%, whereby the pieces of barnyard grass were subjected to surface sterilization. The surface-sterilized pieces of barnyard grass were washed three times with distilled water and then placed on a plate with nutrient-free agar medium. The static cultivation was carried out at 25° C. for 72 hours. Hyphae of mold fungi thus grown were subjected to single hyphae isolation under a microscope, followed by purification on a nutrient medium. Of these, the promising strains, MH-0015, MH-0042, MH-0060, MH-0122, MH-1889, MH-2653, MH-2679, MH-2781, MH-2883, MH-2895, MH-4415, MH-4418, MH-5011, MH-5017, MH-5018, MH-5511 and MH-9011 strains have been deposited under the Budapest treaty with Fermentation Research Institute, Agency of Industrial Science and Technology, Ministry of International Trade and Industry (FRI), 1-3 Higashi 1-chome, Tsukuba-shi, Ibaraki-ken 305, Japan. Their deposit numbers and the like are shown in a list to be described subsequently. With respect to the mold fungi so isolated, their pathogenecity against barnyard grass and their safety to rice were tested.

2) Test for herbicidal activities of isolated microorganisms against barnyard grass and rice plant:

Barnyard grass and rice were allowed to grow to the 1.5 leaf stage in test tubes to provide test samples. Namely, barnyard grass seeds and rice seeds were dipped for 1–2 seconds in a 70% ethyl alcohol solution and then for 10 minutes in sodium hypochlorite solution having an effective chlorine concentration of 2%, whereby the seeds were subjected to surface sterilization. The seeds were then washed three times with distilled water. The sterilized seeds were then planted in test tubes which contained B5 agar medium of the below-described composition and were allowed to grow in a plant growth chamber.

| Composition of B5 Medium | | | | | |
|---|---|---|---|---|---|
| Macroelement | mg/l | mM | Microelement | mg/l | mM |
| KNO$_3$ | 2500 | 25 | KI | 0.75 | 4.5 |
| CaCl$_2$.2H$_2$O | 150 | 1.0 | H$_3$BO$_3$ | 3.0 | 50 |
| MgSO$_4$.7H$_2$O | 250 | 1.0 | MnSO$_4$.H$_2$O | 10 | 60 |
| (NH$_4$)$_2$SO$_4$ | 134 | 1.0 | ZnSO$_4$.7H$_2$O | 2.0 | 7.0 |
| NaH$_2$PO$_4$.H$_2$O | 150 | 1.1 | Na$_2$MoO$_4$.2H$_2$O | 0.25 | 1.0 |
| Vitamin | mg/l | | CuSO$_4$.5H$_2$O | 0.025 | 0.1 |
| Inositol | 100 | | CoCl$_2$.6H$_2$O | 0.025 | 0.1 |
| Nicotinic acid | 1.0 | | Na$_2$.EDTA | 37.3 | 100 |
| Pyridoxine | 1.0 | | FeSO$_4$.7H$_2$O | 27.8 | 100 |
| Thiamine | 10.0 | | Sugar | 20 g/l | |
| | | | pH | 5.5 | |

On the other hand, the isolated microorganisms were subjected to plate culture on separate layers of a potato-dextrose agar culture medium, respectively. The layers were punched out by a sterilized cork borer to obtain mycerial discs as seed cell sources.

The mycerial discs were separately placed on the liquid culture medium in the test tubes in which barnyard grass seedlings and rice seedlings were grown.

After incubating them for 10 days in a plant growth chamber, the pathogenecity of each microorganism against barnyard grass and rice was evaluated in accordance with the following 4-stage system ranging from 0 to 3. The results are summarized in Table 1.

3 Death
2 Severe inhibition to the growth
1 Some inhibition to the growth
0 No effect Incidentally, MH-0003, MH-0007 and MH-0011 strains are Drechslera, Phoma and Fusarium strains, respectively. They were all tested for comparison.

TABLE 1

| Pathogenecity of Isolated Drechslera spp | | |
|---|---|---|
| Microorganism | Barnyard grass | Rice |
| MH-0003 | 0 | 0 |
| MH-0007 | 0 | 3 |
| MH-0011 | 3 | 3 |
| MH-0015 | 3 | 0 |
| MH-0042 | 3 | 0 |
| MH-0060 | 3 | 0 |
| MH-0122 | 3 | 0 |
| MH-1889 | 3 | 0 |
| MH-2653 | 3 | 0 |
| MH-2679 | 3 | 0 |
| MH-2781 | 3 | 0 |
| MH-2883 | 3 | 0 |
| MH-2895 | 3 | 0 |
| MH-2990 | 3 | 0 |
| MH-2998 | 3 | 0 |
| MH-4415 | 3 | 0 |
| MH-4418 | 3 | 0 |
| MH-5011 | 3 | 0 |
| MH-5017 | 3 | 0 |
| MH-5018 | 3 | 0 |
| MH-5511 | 3 | 0 |
| MH-9011 | 3 | 0 |
| Untreated | 0 | 0 |

3) Identification of microorganisms

Identification was conducted with respect to the strains which exhibited marked pathogenecity against barnyard grass but were not recognized at all to have effects on rice. As a result, each of MH-0015, MH-1889, MH-2653, MH-2679, MH-4415, MH-4418, MH-5011, MH-5017, MH-5018, MH-5511 and MH-9011 strains gave a colony as large as 65-75 nun in diameter and showed irregular growth when subjected to plate culture at 28° C. for 7 days on a malt-agar medium. Those colonies had a grayish black in width and 87.5-137.5 μm in length. They had a somewhat bent shape. The conidia had 9 septa at the maximum and 5-7 septa mostly. Conidiophores had a straight shape. From the above characteristics, MH-0015, MH-1889, MH-2653, MH-2679, MH-4415, MH-4418, MH-5011, MH-5017, MH-5018, MH-5511 and MH-9011 strains were all identified as strains of Drechslera monoceras.

MH-0042, MH-0060 and MH-2883 strains had conidia which contained no scar and had a size of 17-22 μm in width and 40-90 μm in length. Regarding the shape of the conidia, some bent, cylindrical conidia were observed. The conidia contained 1-5 septa. From the foregoing characteristics, MH-0042, MH-0060 and MH-2883 strains were identified as strains of Drechslera ravenelii.

Each of MH-0122, MH-2781 and MH-2895 strains gave a colony as large as 20-25 mm in diameter when subjected to plate culture at 28° C. for 7 days on a malt-agar medium. The colony had a bright gray color, but was grayish green at a central part thereof and grayish black on the back. Its conidia were free of scars and had a size of 20-25 μm in width and 55-95 μm in length. The conidia contained 5-6 septa. Conidiophores had a straight shape. From the above characteristics, MH-0122, MH-2781 and MH-2895 strains were identified as strains of Drechslera poae.

Further, MH-2990 and MH-2998 strains were identified as strains of Drechslera spp. in view of the shapes of their colonies and conidia.

On the other hand, MH-0003 strain, MH-0011 strain and MH-0007 strain, which did not show selective pathogenecity against barnyard grass only, but not on rice, were identified as a strain of Drechslera spp., a strain of Fusarium spp. and a strain of Phoma spp., respectively.

The above identification was conducted with reference to M. B. Ellis, "Demariaceus Hyphomycetes", 608 Commonwealth Mycological Institute, Kew, England (1971) and M. B. Ellis, "More Demariaceus Hyphomycetes", 507, Commonwealth Mycological Institute, Kew, England (1976).

The Drechslera strains according to the present invention are not described as pathogens in the Pathogens Safety Control Guideline compiled by the National Institutes of Health (Japan) and are believed to be safe to mammals.

EXAMPLE 2

Control Effects of Drechslera Strains against Barnyardgrass

Each Drechslera strain isolated from the nature inoculated on an oatmeal-agar medium, followed by static culture at 25° C. for 7 days. Aerial hyphae were then removed with distilled water to promote formation of conidia. The conidia so obtained were suspended in a 0.02% "Triton X-100" (trade name; product of Rohm & Haas Co. ) solution to give concentrations of $10^8$ spores/ml and $10^5$ spores/ml, thereby preparing weed control agents containing the Drechslera strain as an effective ingredient.

On the other hand, barnyard grass and rice (varieties: "Nipponbare") were seeded in lowland soil which was contained in 1/10000-are pots, and were reared to the 1.5 leaf stage respectively. After the pots were irrigated to keep the seedlings under submerged conditions of about 3 cm in water depth, the above weed control agents containing conidia of the Drechslera strain were separately applied dropwise in an amount of 5 ml per pot. After the seedlings were reared for 10 days in a weather-controlled room which was maintained at 30° C. during the day time and at 25° C. at night, effects of the Drechslera strain on barnyard grass and rice were evaluated in accordance with a similar standard to Test 1. The results are shown in Table 2.

3 Death
2 Severe inhibition to the growth
1 Some inhibition to the growth
0 No effect

TABLE 2

| Selective herbicidal Activities of Drechslera spp. - Pot Test | | | | |
|---|---|---|---|---|
| | Barnyard grass | | Rice | |
| Microorganism | $10^8$ | $10^5$ | $10^8$ | $10^5$ |
| MH-0015 | 2 | 1 | 0 | 0 |
| MH-0042 | 2 | 0 | 0 | 0 |
| MH-0060 | 2 | 0 | 0 | 0 |
| MH-0122 | 2 | 0 | 0 | 0 |
| MH-1889 | 3 | 1 | 0 | 0 |
| MH-2653 | 2 | 1 | 0 | 0 |

TABLE 2-continued

Selective herbicidal Activities of Drechslera spp. - Pot Test

| Microorganism | Barnyard grass $10^8$ | Barnyard grass $10^5$ | Rice $10^8$ | Rice $10^5$ |
|---|---|---|---|---|
| MH-2679 | 2 | 0 | 0 | 0 |
| MH-2781 | 2 | 0 | 0 | 0 |
| MH-2883 | 2 | 0 | 0 | 0 |
| MH-2895 | 2 | 0 | 0 | 0 |
| MH-2990 | 2 | 0 | 0 | 0 |
| MH-2998 | 2 | 0 | 0 | 0 |
| MH-4415 | 3 | 3 | 0 | 0 |
| MH-4418 | 3 | 3 | 0 | 0 |
| MH-5011 | 3 | 3 | 0 | 0 |
| MH-5017 | 3 | 3 | 0 | 0 |
| MH 5018 | 3 | 3 | 0 | 0 |
| MH-5511 | 3 | 3 | 0 | 0 |
| MH-9011 | 3 | 3 | 0 | 0 |
| Untreated | 0 | 0 | 0 | 0 |

As a result of the test, MH-4415, MH-4418, MH-5011, MH-5017, MH-5018, MH-5511 and MH-9011 strains of Drechslera spp., said strains all pertaining to the present invention, showed herbicidal effects against barnyard grass which were as much as 100–1,000 times superior to MH-0015 to MH-2998 strains. Further, their safety to rice was also observed.

EXAMPLE 3

In a similar manner to Example 2, pathogenecity of each microorganism accoridng to the present invention against various species of Echinochloa spp., wheat, barley, corn and rice was evaluated. Tested as barnyard grass were Echinochloa colonum, Echinochloa oryzicola, Echinochloa crus-galli var. formosensis, Echinochloa crus-galli vat. crus-galli and Echinochloa crus-galli vat. praticola. Tested as rice were "Nioppon-bare", "Sasanishiki" and "Koshihikari", which are rice species cultivated. Pathogenecity of each microorganism according to the present invention against the barnyard grass and rice was evluated 10 days after the inoculation. The results are shown in Tables 3-1 and 3-2.

TABLE 3-1

Pathogenectiy of Invention Microorganisms against Various Echinochloa spp.

| Microorganism | Barnyard grass | | | | | Rice | | |
| | Echinochloa oryzicola | Echinochloa crus-galli var. formosensis | Echinochloa crus-galli var. crus-galli | Echinochloa crus-galli var. praticola | Echinochloa colonum | Nipponbare | Sasanishiki | Koshihikari |
|---|---|---|---|---|---|---|---|---|
| MH0015 | 0 | 3 | 3 | 3 | 3 | 0 | 0 | 0 |
| MH2653 | 1 | 3 | 3 | 3 | 3 | 0 | 0 | 0 |
| MH4418 | 3 | 3 | 3 | 3 | 3 | 0 | 0 | 0 |
| MH5011 | 3 | 3 | 3 | 3 | 3 | 0 | 0 | 0 |
| MH5017 | 3 | 3 | 3 | 3 | 3 | 0 | 0 | 0 |
| MH5018 | 3 | 3 | 3 | 3 | 3 | 0 | 0 | 0 |
| MH5511 | 3 | 3 | 3 | 3 | 3 | 0 | 0 | 0 |
| MH9011 | 3 | 3 | 3 | 3 | 3 | 0 | 0 | 0 |
| Untreated | 0 | 0 | 0 | 0 | 0 | 0 | 0 | 0 |

3: Death,
2: Marked inhibition to the growth,
1: Some inhibition to the growth,
0: No effect.

TABLE 3-2

Pathogenecity of Invention Microorganisms against Various Echinochloa spp.

| Microorganism | Wheat | Barley | Corn |
|---|---|---|---|
| MH-0015 | 0 | 0 | 0 |
| MH-2653 | 0 | 0 | 0 |
| MH-4418 | 0 | 0 | 0 |
| MH-5011 | 0 | 0 | 0 |
| MH-5017 | 0 | 0 | 0 |
| MH-5518 | 0 | 0 | 0 |
| MH-5511 | 0 | 0 | 0 |
| MH-9011 | 0 | 0 | 0 |
| Untreated | 0 | 0 | 0 |

As a result of the test, MH-4418, MH-5011, MH-5017, MH-5018, MH-5511 and MH-9011 strains of Drechslera monoceras, said strains pertaining to the present invention, had high pathogenecity against all the species and varieties of Echinochloa spp. and showed excellent herbicidal effects against them. Further, their safety to rice, wheat, barley and corn was also obserbed.

EXAMPLE 4

Formulation Method of Weed Control Compositions Containing Living Fungal Cells of Drechslera spp. and Weed Control Method by the Compositions The 6 strains of Drechslera spp. isolated above were separately inoculated on an oatmeal-agar medium and then subjected to static culture at 25° C. for 7 days. Aerial hyphae were then removed with distilled water, thereby obtaining spores. They were separately suspended at a concentration of $10^6$ spores/ml in a 0.05% "Triton X-100" (trade name) solution, whereby weed control compositions containing, as an effective ingredient, living fungal cells of the respective strains of Drechslera spp. were formualted.

On the other hand, seeds of barnyard grass and rice were planted in soil which was contained PVC pots having a diameter of 10 cm and were reared to seedlings of the 1.5 leaf stage respectively. The weed control compositions were separately applied dropwise into the pots under irrigation so as to inoculate $10^7$ spores of the strains of Drechslera spp. per pot. The pots were maintained at 30° C. during the daytime and at 25° C. at night. Rearing was conducted for 20 days in a weather-controlled room. The results are shown in Table 4.

TABLE 4

Selective Herbicidal Effects of Weed Control Compositions Containing Living Fungal Cells of Drechslera spp.

| Microorganism | Barnyard grass | Rice |
|---|---|---|
| MH-0015 | 3 | 0 |
| MH-0042 | 3 | 0 |
| MH-0060 | 3 | 0 |

TABLE 4-continued

Selective Herbicidal Effects of Weed
Control Compositions Containing
Living Fungal Cells of Drechslera spp.

| Microorganism | Barnyard grass | Rice |
|---|---|---|
| MH-0122 | 3 | 0 |
| MH-2653 | 3 | 0 |
| MH-2679 | 3 | 0 |

Note:
3 Death
2 Marked inhibition to the growth
1 Some inhibition to the growth
0 No effect As a result of the test, the pathogens useful in the practice of this invention, namely, Drechslera spp. MH-0015, MH-0042, MH-0060, MH-0122, MH-2653 and MH-2679 showed high pathogenecity against banyard grass and effects to rice seedlings were not observed at all.

EXAMPLE 5

Formulation Method of Weed Control Composition Containing as Effective Ingredient *Drechslera monoceras* MH-2653 and Weed Control Method Using the Composition Inoculated on 100 ml of a potato-dextrose liquid culture medium was a seed culture of the pathogen useful in the practice of this invention, Drechslera monoceras MH-2653, followed by culture at 25° C. for 7 days. After the culture, obtained mycelia were homogenized in culture medium, and spread on a filter paper and then standed for 3 days to form spores. Using those spores, a weed control composition was formulated in a similar manner to Example 4.

On the other hand, 50 barnyard grass seeds were planted in each of three 1/5000-a Wagner pots and were allowed to grow to the 1.5 leaf stage. Into the pots under irrigation, the weed control composition was applied dropwise so as to inoculate the pots with $10^5$, $10^6$, $10^7$ and $10^8$ spores of Drechslera monoceras MH-2653, respectively. They were reared in a green house whose temperature was controlled within a range of from 15° C. to 35° C. Herbicidal activities were determined based on the percentage of dead seedlings. The result are shown in Table 5.

As a result of the test, Drechslera monoceras MH-2653 useful in the practice of this invention shows excellent herbicidal activities against barnyard grass.

TABLE 5

Effects of spore dosage on herbicidal activity of Drechslera spp. MH-2653

| Inoculum size (spores/pot) | Control value (%) |
|---|---|
| 0 | 0 |
| $1 \times 10^5$ | 54 |
| $1 \times 10^6$ | 86 |
| $1 \times 10^7$ | 100 |
| $1 \times 10^8$ | 100 |

EXAMPLE 6

Formulation Method of Weed Control Composition Containing Metabolite of Drechslera spp. and Weed Control Method by the Composition Isolated 6 strains of Drechslera spp. were separately subjected to standing culture at 25° C. for 10 days, each, on 100 ml of a potato-dextrose liquid culture medium. Thereafter, mat-like mycelium samples thus obtained were separately homogenized in a liquid culture medium. The resulting culture broths were separately filtered through a membrane filter and the flitrates were separately concentrated for use as weed control compositions.

On the other hand, barnyard grass seeds were subjected to surface sterilization in a similar manner to the herbicidal activity test in Example 1 and then planted in portions in test tubes which contained 5 ml of a nutrient-free liquid culture medium. They were reared until the 1.5 leaf stage in a plant-growth chamber. The liquid weed control compositions were separately applied at a rate of 0.5 ml into the test tubes with the barnyard grass seedlings reared therein. The seedlings were reared for 10 days, and the herbicidal activities of the individual compositions were determined. The results are shown in Table 6.

TABLE 6

Herbicidal Activities of Weed Control
Compositions Containing Metabolite of
Drechslera spp. against Barnyard Grass

| Microorganism | Herbicidal activities |
|---|---|
| MH-0001 | 0 |
| MH-0007 | 0 |
| MH-0015 | 3 |
| MH-0042 | 3 |
| MH-0060 | 2 |
| MH-0122 | 2 |
| MH-2653 | 3 |
| MH-2679 | 3 |

Note:
3; Death
2; Marked inhibition to the growth
1; Some inhibition to the growth
0; No effect As a result of the test, the metabolites of Drechslera spp. MH-0015, MH-0042, MH-0060, MH-0122, MH-2653 and MH-2679 showed marked hericidal activities against barnyard grass.

EXAMPLE 7

Pathogenecity Test of Drechslera spp. for Primary Crops

Pathogens Drechslera spp. useful in the practice of this invention were found to have no pathogenecity against economic crops. In a manner similar to Example 5, the test was conducted using rice, wheat, barley and corn as target plants. The results are shown in Table 7.

TABLE 7

Pathogenecity of Drechslera spp. against Primary Crops

| Microorganism | Rice | Wheat | Barley | Corn |
|---|---|---|---|---|
| MH-0015 | 0 | 0 | 0 | 0 |
| MH-0042 | 0 | 0 | 0 | 0 |
| MH-0060 | 0 | 0 | 0 | 0 |
| MH-0122 | 0 | 0 | 0 | 0 |
| MH-2653 | 0 | 0 | 0 | 0 |
| MH-2679 | 0 | 0 | 0 | 0 |

Note:
3; Death
2; Maked inhibition ot the growth
1; Some inhibition to the growth
0; No effect As a result of the test, Drechslera spp. useful in the practice of this invention were found to have absolutely no pathogenecity against rice, wheat, barley and corn. These microorganisms of this invention were hence recognized to be usable as mycoherbicides.

EXAMPLE 8

Effects of Chemical Herbicides on Various Biological Properties of Drechslera spp.

Mycerial discs of each strain of Drechslera spp., said discs having been prepared by the method described in Exmaple 1, were separately placed on layers of a potato-dextrose agar medium, which contained chemical herbicides such as CNP (Herbicide A in tables), mefenacet (Herbicide E in tables), pretilachlor (Herbicide I in tables), benthiocarb (Herbicide L in tables) and bensulfuron (Herbicide P in tables) at the concentration of 500 ppm, respectively. Static culture was then conducted at 25° C. for 5 days. The diameter of each colony so formed was measured and was recorded as a hypha length. Further, spores in aqueous "Triton X-100" solutions of spore suspensions of each strain of Drechslera spp., said solutions having been prepared by the method described in Example 2, were resuspended in portions of a potato-dextrose liquid medium, which contained the individual chemical herbicides-at the concentration of 500 ppm, respectively. Shaking culture was then conducted at 25° C. for 24 hours. After the culture, spore germination was microscopically observed to calculate the rate of spore germination. Effects of each chemical herbicide on the growth of hyphae and the rate of spore germination of each strain of Drechslera spp. are expressed in terms of percentage relative to a corresponding control group which did not contain the chemical herbicide. The results are shown in Tables 8-1 and 8-2.

As is apparent from Tables 8-1 and 8-2, neither hyphal growth inhibition nor spore germination inhibition by the chemical herbicides was practically observed with respect to the Drechslera strains according to the present invention.

TABLE 8-1

Effects of Chemical Herbicides against Hyphal Growth of Drechslera spp.

| Microorganism | Chemical herbicide | | | |
|---|---|---|---|---|
|  | A | E | I | L |
| MH-0015 | 98 | 96 | 85 | 93 |
| MH-0042 | 99 | 98 | 83 | 93 |
| MH-0060 | 101 | 95 | 84 | 92 |
| MH-0122 | 103 | 98 | 87 | 98 |
| MH-1889 | 100 | 100 | 90 | 100 |
| MH-2653 | 99 | 95 | 86 | 96 |
| MH-2679 | 100 | 96 | 84 | 95 |
| MH-2781 | 103 | 98 | 88 | 99 |
| MH-2883 | 105 | 100 | 88 | 98 |
| MH-2895 | 102 | 100 | 86 | 96 |
| MH-2990 | 99 | 94 | 86 | 97 |
| MH-2998 | 98 | 96 | 82 | 93 |
| MH-4415 | 100 | 100 | 98 | 100 |
| MH-4418 | 98 | 98 | 88 | 100 |
| MH-5011 | 96 | 100 | 92 | 100 |
| MH-5017 | 100 | 98 | 90 | 98 |
| MH-5018 | 100 | 100 | 95 | 100 |
| MH-5511 | 100 | 100 | 98 | 100 |
| MH-9011 | 98 | 98 | 90 | 100 |

TABLE 8-2

Effects of Chemical Herbicides against Spore Germination of Drecslera spp.

| Microorganism | Chemical herbicide | | | | |
|---|---|---|---|---|---|
|  | A | E | I | L | P |
| MH-0015 | 95 | 97 | 88 | 83 | 100 |
| MH-0042 | 98 | 98 | 85 | 85 | 99 |
| MH-0060 | 99 | 94 | 84 | 84 | 101 |
| MH-0122 | 100 | 99 | 86 | 87 | 98 |
| MH-1889 | 98 | 100 | 90 | 92 | 98 |
| MH-2653 | 100 | 95 | 88 | 85 | 103 |
| MH-2679 | 99 | 97 | 85 | 86 | 100 |
| MH-2781 | 97 | 99 | 89 | 88 | 96 |
| MH-2883 | 102 | 98 | 88 | 89 | 101 |
| MH-2895 | 99 | 100 | 87 | 88 | 104 |
| MH-2990 | 100 | 96 | 88 | 86 | 98 |
| MH-2998 | 98 | 98 | 89 | 85 | 102 |
| MH-4415 | 101 | 98 | 90 | 95 | 100 |
| MH 4418 | 100 | 98 | 98 | 90 | 102 |
| MH-5011 | 98 | 92 | 90 | 88 | 98 |
| MH-5017 | 100 | 98 | 95 | 87 | 99 |
| MH-5018 | 100 | 98 | 90 | 85 | 95 |
| MH-5511 | 105 | 100 | 95 | 90 | 100 |
| MH-9011 | 102 | 100 | 98 | 95 | 102 |

EXAMPLE 9

Control Effects of Compositions of Drechslera Strain and Chemical Herbicide CNP on Barnyard Grass Each Drechslera strain isolated from the nature was inoculated to an oatmeal agar medium, followed by static culture at 25° C. for 7 days. Aerial hyphae were then removed with distilled water to promote formation of conidia. The conidia so obtained were suspended in a 0.02% "Triton X-100" (trade name; product of Rohm & Haas Co.) solution to give prescribed concentrations, thereby preparing weed control agents containing the Drechslera strain as an effective ingredient.

Regarding CNP, its 9% granular formulation was weighed in the amounts of 30-1 mg to use it as a chemical herbicide.

On the other hand, barnyard grass and rice (varieties: "Nipponbare") were seeded in lowland soil which was contained in 1/10000-are pots, and were reared to the 1.5 leaf stage respectively. After the pots were irrigated to keep the seedlings under submerged conditions of about 3 cm in water depth, the above weed control agents containing conidia of the Drechslera strain were separately applied dropwise in an amount of 5 ml per pot. At the same time, each pot was treated with the chemical herbicide CNP. After the seedlings were reared for 10 days in a weather-controlled room which was maintained at 30° C. during the day time and at 25° C. at night, effects of the Drechslera strain and the chemical herbicide on the barnyard grass and rice were evaluated in accordance with a similar standard to Example 1. The results are shown in Table 9.

3 Death
2 Severe inhibition to the growth
1 Some inhibition to the growth
0 No effect Although the results of Table 9 are only one example, the Drechslera strain and the chemical herbicide exhibited significant synergistic effects in each combination.

TABLE 9

Synergistic Effects of Drechslera spp. and Chemical Herbicides

| Microorganism/ 1/1000 are | C N P (mg) | | | | |
|---|---|---|---|---|---|
|  | 30 | 10 | 3 | 1 | 0 |
| 1 × 10$^6$ spores | 100 | 100 | 100 | 100 | 100 |
|  | (0) | (0) | (0) | (0) | (0) |
| 3 × 10$^5$ spores | 100 | 100 | 100 | 100 | 80 |
|  | (0) | (0) | (0) | (0) | (0) |

TABLE 9-continued

Synergistic Effects of Drechslera spp. and Chemical Herbicides

| Microorganism/ | C N P (mg) | | | | |
|---|---|---|---|---|---|
| 1/1000 are | 30 | 10 | 3 | 1 | 0 |
| $1 \times 10^5$ spores | 100 | 100 | 100 | 100 | 50 |
|  | (0) | (0) | (0) | (0) | (0) |
| $3 \times 10^4$ spores | 100 | 100 | 100 | 70 | 35 |
|  | (0) | (0) | (0) | (0) | (0) |
| $1 \times 10^4$ spores | 100 | 90 | 60 | 50 | 15 |
|  | (0) | (0) | (0) | (0) | (0) |
| 0 spore | 100 | 60 | 35 | 20 | 0 |
|  | (0) | (0) | (0) | (0) | (0) |

Barnyard grass control value: 0–100%
Sign in parenthisese indicates injury against rice.

Formulation examples and herbicidal activity tests of weed control compositions according to the present invention will next be described.

FORMULATION EXAMPLE 1 (Granular formulation)

After 2 wt.% of "Neopelex" (trade mark; product of Kao Corporation), 2 wt.% of "Sun Ekis P252" (trade name; product of Sanyo-Kokusaku Pulp Co., Ltd.) and 96 wt.% of zeolite were thoroughly mixed, a spore suspension containing $10^9$ conidia of Drechslera MH-5018 per gram of a granular formulation to be formulated was added to the resultant mixture to moisten the same. The thus-moistened mass was then extruded. into granules by a small extruder. The granules were dried in air, crushed and then processed by a shifting machine, whereby granules of 0.3–2 mm were obtained.

FORMULATION EXAMPLE 2 (Granular formulation)

After 2 wt.% of "Neopelex" (trade mark; product of Kao Corporation), 2 wt.% of "Sun Ekis P252" (trade name; product of Sanyo-Kokusaku Pulp Co., Ltd.) and 96 wt.% of zeolite were thoroughly mixed, a spore suspension containing $10^8$ conidia of Drechslera MH-5511 per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

FORMULATION EXAMPLE 3 (Granular formulation)

After 2 wt.% of "Neopelex" (trade mark; product of Kao Corporation), 2 wt.% of "Sun Ekis P252" (trade name; product of Sanyo-Kokusaku Pulp Co., Ltd.) and 96 wt.% of zeolite were thoroughly mixed, a spore suspension containing $10^9$ conidia of Drechslera MH-9011 per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

FORMULATION EXAMPLE 4 (Wettable powder)

A mixture of 2 wt.% of "Neopelex" (trade mark; product of Kao Corporation), 2 wt.% of Triton (X-100) and 5 wt.% of white carbon was impregnated with a spore suspension containing $10^9$ conidia of Drechslera MH-4418 per gram of a wettable powder to be formulated, followed by drying in air. Diatomaceous earth (91 wt.%) was then added, followed by thorough mixing and grinding to obtain the wettable powder.

FORMULATION EXAMPLE 5 (Wettable powder)

A mixture of 2 wt.% of "Neopelex" (trade mark; product of Kao Corporation; sodium dodecylbenzenesulfonate), 1 wt.% of "Neugen EA 80" (trade name, product of Sanyo Chemical Industries, Ltd.; polyoxyethylenenonylphenyl ether), 5 wt.% of white carbon and 92 wt.% of diatomaceous earth was impregnated with a spore suspension containing $10^9$ conidia of Drechslera MH-5511 per gram of a wettable powder to be formulated, followed by drying in air. The resultant mixture was thoroughly mixed and ground to obtain the wettable powder.

FORMULATION EXAMPLE 6 ( Flowable formulation)

"Sun Ekis P252" (10 wt.%) dissolved in 80 wt.% of water was wet-ground, followed by the addition of 0.4 wt.% of "Kelzan S" (trade name; product of Kelco Corp.) dissolved in 9.6 wt.% of a spore suspension which contained $10^{10}$ conidia of Drechslera MH-5017 per gram of a flowable formulation to be obtained. The resultant mixture was mixed to obtain the flowable formulation.

FORMULATION EXAMPLE 7 (Flowable formulation)

After 10 wt.% of "Sun Ekis P252" (trade name; described above) dissolved in 70 wt.% of water was mixed with 10 wt.% of a spore suspension which contained 10 conidia of Drechslera MH-5511 per gram of a flowable formulation to be obtained, the resultant mixture was wet-ground. Then, 0.2 wt.% of "Kelzan S" (trade name; product of Kelco Corp.; xanthan gum) dissolved in 9.8 wt.% of water was added to obtain the flowable formulation.

FORMULATION EXAMPLE 8 (Dry flowable formulation)

Sodium alkylbenzenesulfonate (15 wt.%), polypropylene glycol polyethylene glycol ether (85 wt.%) and $10^{10}$ conidia of Drechslera MH-5011 per gram of a dry flowable formulation to be obtained were mixed to obtain the dry flowable formulation.

FORMULATION EXAMPLE 9 (Dust)

"Emulgen 910" (trade name; product of Kao Corporation; polyoxyethylenenonyl phenyl ether; 0.5 wt.%) and kaolin clay (99.5 wt.%) were thoroughly ground and mixed, followed by the addition of $10^8$ conidia of Drechslera MH-9011 per gram of a dust to be obtained. The dust was hence obtained.

FORMULATION EXAMPLE 10 (Emulsion)

In a mixture of 5 wt.% of lecithin and 94 wt.% of heavy white oil, $10^{10}$ conidia of Drechslera MH-5511 were suspended per gram of an emulsion to be formulated. An equiamount of 1 wt.% Triton X-100 was added to the suspension. The resultant mixture was mixed and emulsified to obtain the emulsion.

FORMULATION EXAMPLE 11 (Granular formulation)

After 9 wt.% of the finely ground chemical herbicide, CNP (Herbicide A in tables), 2 wt.% of "Neopelex" (trade mark; product of Kao Corporation), 2 wt.% of "Sun Ekis P252" (trade name; product of Sanyo-Kokusaku Pulp Co., Ltd.) and 87 wt. % of zeolite were thoroughly mixed, a spore suspension containing $10^8$ conidia of Drechslera MH-5018 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

FORMULATION EXAMPLE 12 (Granular formulation)

After 3.5 wt.% of the chemical herbicide, butachlor (Herbicide H in tables), 2 wt.% of "Neopelex" (trade mark; product of Kao Corporation), 2 wt.% of "Sun Ekis P252" (trade name; product of Sanyo-Kokusaku Pulp Co., Ltd.) and 92.5 wt.% of zeolite were thoroughly mixed, a spore suspension containing $10^8$ conidia of MH-5511 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

FORMULATION EXAMPLE 13 (Granular formulation)

After 4 wt.% of the finely ground chemical herbicide, mefenasate (Herbicide E in tables), 2 wt.% of "Neopelex" (trade mark; product of Kao Corporation), 2 wt. % of "Sun Ekis P252" (trade name; product of Sanyo-Kokusaku Pulp Co., Ltd.) and 92 wt.% of zeolite were thoroughly mixed, a spore suspension containing $10^8$ conidia of Drechslera MH-5511 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

FORMULATION EXAMPLE 14 (Granular formulation)

After 0.2 wt.% of the finely ground chemical herbicide, bensulfuron (Herbicide P in tables), 2 wt.% of "Neopelex" (trade mark; product of Kao Corporation), 2 wt.% of "Sun Ekis P252" (trade name; product of Sanyo-Kokusaku Pulp Co., Ltd.) and 95.8 wt.% of zeolite were thoroughly mixed, a spore suspension containing $10^8$ conidia of Drechslera MH-5511 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

FORMULATIONE EXAMPLE 15 (Granular formulation)

After 0.3 wt.% of the finely ground chemical herbicide, pyrazosulfron ethyl (Herbicide Q in tables), 2 wt.% of "Gosenol GL-05s" (product of The Nippon Synthetic Chemical Industry Co., Ltd.; PVA), 2 wt.% of "Sun Ekis P252" (trade name; product of Sanyo-Kokusaku Pulp Co., Ltd.; sodium lignin sulfonate) and 95.7 wt.% of clay were thoroughly mixed, a spore suspension containing $10^8$ conidia of Drechslera MH-9011 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

FORMULATION EXAMPLE 16 (Granular formulation)

After 0.3 wt.% of the finely ground chemical herbicide, oxadiazon (Herbicide D in tables), 2 wt.% of "Gosenol GL-05s" (product of The Nippon Synthetic Chemical Industry Co., Ltd.; PVA), 2 wt.% of "Sun Ekis P252" (product of Sanyo-Kokusaku Pulp Co., Ltd.; sodium lignin sulfonate) and 94.5 wt.% of clay were thoroughly mixed, a spore suspension containing $10^8$ conidia of Drechslera MH-4418 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

FORMULATION EXAMPLE 17 (Granular formulation)

After 1.5 wt.% of the finely ground chemical herbicide, simetryne (Herbicide S in tables), 2 wt.% of "Gosenol GL-05s" (product of The Nippon Synthetic Chemical Industry Co., Ltd.; PVA), 2 wt.% of "Sun Ekis P252" (product of Sanyo-Kokusaku Pulp Co., Ltd.; sodium lignin sulfonate) and 94.5 wt.% of clay were thoroughly mixed, a spore suspension containing $10^8$ conidia of Drechslera MH-1889 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

FORMULATION EXAMPLE 18 (Granular formulation)

After 6 wt.% of the chemical herbicide, molinate (Herbicide N in tables), 2 wt.% of "Neopelex" (trade mark; product of Kao Corporation), 2 wt.% of "Sun Ekis P252" (product of Sanyo-Kokusaku Pulp Co., Ltd.; sodium lignin sulfonate) and 90 wt.% of zeolite were thoroughly mixed, a spore suspension containing $10^8$ conidia of Drechslera MH-5017 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

FORMULATION EXAMPLE 19 (Wettable powder)

A mixture of 30 wt.% of the chemical herbicide, chlormethoxynil (Herbicide B in tables), 2 wt.% of "Neopelex" (trade mark; product of Kao Corporation), 2 wt.% of Triton (X-100) and 5 wt.% of white carbon was impregnated with a spore suspension containing $10^9$ conidia of Drechslera MH-4415 per gram of a wettable powder to be formulated. Air-dried diatomaceous earth (61 wt.%) was then added to the mixture so impregnated. They were then thoroughly ground to obtain the wettable powder.

FORMULATION EXAMPLE 20 (Wettable powder)

A mixture of 40 wt.% of the chemical herbicide, propanil (Herbicide J in tables), 2 wt.% of "Neopelex" (trade mark; product of Kao Corporation), 2 wt.% of Triton (X-100) and 5 wt.% of white carbon was impregnated with a spore suspension containing $10^9$ conidia of Drechslera MH-5511 per gram of a wettable powder to be formulated. Air-dried diatomaceous earth (51 wt.%) was then added to the mixture so impregnated- They were then thoroughly ground to obtain the wettable powder.

FORMULATION EXAMPLE 21 (Wettable powder)

A mixture of 20 wt.% of the chemical herbicide, benthiocarb (Herbicide L in tables), 2 wt.% of "Neopelex" (trade mark; product of Kao Corporation), 2 wt.% of Triton (X-100) and 5 wt.% of white carbon was impregnated with a spore suspension containing $10^9$ conidia of Drechslera MH-5018 per gram of a wettable powder to be formulated. Air-dried diatomaceous earth (71 wt.%) was then added to the mixture so impregnated. They were then thoroughly ground to obtain the wettable powder.

FORMULATION EXAMPLE 22 (Wettable powder)

A mixture of 40 wt.% of the chemical herbicide, naproanilide (Herbicide F in tables), 2 wt.% of "Neopelex" (trade mark; product of Kao Corporation; sodium dodecylbenzenesulfonate), 1 wt.% of "Neugen EA 80" (trade name, product of Sanyo Chemical Industries, Ltd.; polyoxyethylenenonylphenyl ether) , 5 wt. % of white carbon and 52 wt.% of diatomaceous earth was impregnated with a spore suspension containing $10^9$ conidia of Drechslera MH-2653 per gram of a wettable powder to be formulated, followed by thorough mixing and grinding to obtain the wettable powder.

FORMULATION EXAMPLE 23 (Wettable powder)

A mixture of 20 wt.% of the chemical herbicide dimepiperate (Herbicide M in tables) , 2 wt. % of sodium alkylbenzenesulfonate, 1 wt.% of polyoxyethylene alkylphenylether and 77 wt.% of zeaklite was impregnated with a spore suspension containing $10^9$ conidia of Drechslera MH-0122 per gram of a wettable powder to be formulated, followed by thorough mixing and grinding to obtain the wettable powder.

FORMULATION EXAMPLE 24 (Wettable powder)

A mixture of 40 wt.% of the chemical herbicide clomeprop (Herbicide K in tables), 5 wt.% of white carbon, 6 wt.% of polyoxyethylene alkylphenylether ammonium sulfate salt, 2 wt.% of sodium lignin sulfonate and 47 wt.% of diatomaceous earth was thoroughly mixed and ground by a Jet-O-Miser, followed by impregnation with a spore suspension containing $10^9$ conidia of Drechslera MH-0015 per gram of a wettable powder to be formulated. The resultant mixture was thoroughly mixed and ground to obtain the wettable powder.

FORMULATION EXAMPLE 25 (Flowable formulation)

After 45 wt.% of the finely ground chemical herbicide, CNP (Herbicide A in tables) and 10 wt.% of "Sun Ekis P252" dissolved in 35 wt.% of water were mixed and wet-ground, 0.4 wt. % of "Kelzan S" (trade name: product of Kelco Corp. ) dissolved in 9.6 wt.% of a spore suspension containing $10^9$ conidia of Drechslera MH-0042 per gram of a flowable formulation to be formulated was added to the resultant mixture. The thus-obtained mixture was then mixed to obtain the flowable formulation.

FORMULATION EXAMPLE 26 (Flowable formulation)

After 10 wt.% of the chemical herbicide, pretilachlor (Herbicide I in tables) and 10 wt.% of "Sun Ekis P252" dissolved in 70 wt.% of water were mixed and wet-ground, 0.4 wt.% of "Kelzan S" (trade name: product of Kelco Corp.) dissolved in 9.6 wt.% of a spore suspension containing $10^9$ conidia of Drechslera MH-5511 per gram of a flowable formulation to be formulated was added to the resultant mixture. The thus-obtained mixture was then mixed to obtain the flowable formulation.

FORMULATION EXAMPLE 27 (Flowable formulation)

After 56.7 wt.% of water was added to the mixture of 30 wt.% of the chemical herbicide, benthiocarb (Herbicide L in tables), 2 wt.% of sodium lignin sulfonate; 0.3 wt.% of xanthan gum and 1 wt.% of polyoxyethylene alkylarylether, 10 wt.% of a spore suspension containing $10^9$ conidia of Drechslera MH-5017 per gram of a flowable formulation to be formulated was added to the resultant mixture. The thus-obtained mixture was then finely ground by a sand grinder to obtain the flowable formulation.

FORMULATION EXAMPLE 28 (Flowable formulation)

After 30 wt.% of the chemical herbicide, esprocarb (Herbicide 0 in tables), 10 wt.% of "Sun Ekis P252" (trade name; described above) dissolved in 40 wt.% of water and 10 wt.% of a spore suspension containing $10^9$ conidia of Drechslera MH-5011 per gram of a flowable formulation to be formulated were mixed, the resultant mixture was mixed and wet-ground. Then 0.4 wt.% of "Kelzan S" (trade name: product of Kelco Corp.; xanthan gum) dissolved in 9.6 wt.% of water was added to the mixture to obtain the flowable formulation.

FORMULATION EXAMPLE 29 (Dry flowable formulation)

The finely-ground chemical herbicide, pyrazolate (Herbicide R in tables; 60 wt.%), sodium alkylbenzenesulfonate (5 wt.%), polypropylene glycol polyethylene glycol ether (35 wt.%) and $10^9$ conidia of Drechslera 2781 per gram of the chemical herbicide were mixed to obtain the dry flowable formulation.

FORMULATION EXAMPLE 30 (Dust)

The finely-ground chemical herbicide, bensulfuron (Herbicide P in tables; 0.2 wt.%), "Emulgen 910" (trade name; product of Kao Corporation; polyoxyethylenenonyl phenyl ether; 0.5 wt.%) and kaolin clay (99.3 wt.%) were thoroughly mixed and ground, followed by the addition of $10^8$ conidia of Drechslera MH-9011 per gram of a dust to be obtained. The dust was hence obtained.

FORMULATION EXAMPLE 31 (DUST)

The finely-ground chemical herbicide, mefenacet (Herbicide E in tables; 4 wt.%), "Emulgen 910" (trade name; product of Kao Corporation; polyoxyethylenenonyl phenyl ether; 1 wt.%, sodium lignin sulfonate (3 wt.%), polyoxyethylene alkylarylether (2 wt.%) and kaolin clay (90 wt.%) were mixed and ground, followed by the addition of $10^9$ conidia of Drechslera MH-2883 per gram of a dust to be obtained. The dust was hence obtained.

FORMULATION EXAMPLE 32 (Emulsion)

In a mixture of 1 wt.% of the chemical herbicide, bensulfuron (Herbicide P in tables), 5 wt.% of lecithin and 94 wt.% of heavy white oil, $10^9$ conidia of Drechslera MH-5511 were suspended per gram of an emulsion to be formulated. An equiamount of 1 wt.% Triton X-100 was added to the suspension. The resultant mixture was mixed and emulsified to obtain the emulsion.

FORMULATION EXAMPLE 33 (Emulsion)

In a mixture of 2 wt.% of the chemical herbicide, biphenox (Herbicide C in tables), 5 wt.% of lecithin and 92 wt.% of heavy white oil, $10^{10}$ conidia of Drechslera MH-0060 were suspended per gram of an emulsion to be formulated. An equiamount of 1 wt.% Triton X-100 was added to the suspension. The resultant mixture was mixed and emulsified to obtain the emulsion.

In addition to the above formulation examples, formulation was conducted with respect to the combinations of conidia of various strains of Drechslera spp. and various chemical herbicides. It is therefore to be noted that formulations are not limited to those exemplified above.

EXAMPLE 10

Herbicidal Effects of Weed Control Compositions Which Contain Drechslera Strains and Chemical Herbicides in Combination, against Barnyard Grass-Granular Formulations Barnyard grass seeds were planted in 1/1000-are pots contained in lowland soil, and the plants raising from the seeds were reared to the 1.5 leaf stage. The plants were irrigated to keep about 3 cm depth in water and treated with 30 mg (equivalent to one tenth of the standard dosage) of the granular formulations prepared in Formulation Examples 11–18, respectively. The plants were then allowed to grow in a green house which was maintained at 35° C. during the day time and at 20° C. at night. Twenty days after the treatment, the remaining populations in the individual pots were counted. The control values against barnyard grass were calculated in accordance with the following formula and are shown in Tables 10-1 to 10-3.

$$\text{Control value} = \frac{\text{Remaining population in untreated group} - \text{Remaining population in treated group}}{\text{Remaining population in untreated group}} \times 100$$

In the tables, letters A-O represent the following herbicides.

A: CNP
B: Chlormethoxynil
C: Bifenox
D: Oxadiazon
E: Mefenasate
F: Naproanilide
G: NSK-850
H: Butachlor
I: Pretilachlor
J: Propanil
K: Clomeprop
L: Benthiocarb
M: Dimepiperate
N: Molinate
O: Esprocarb

TABLE 10-1

Herbicidal Effects of Drechslera spp.- Diphenyl Ether Chemical Herbicide Compositions

| Microorganism | — | A | B | C | D |
|---|---|---|---|---|---|
| — | 0 | 10 | 25 | 20 | 40 |
| MH-0015 | 10 | 100 | 100 | 100 | 100 |
| MH-0042 | 5 | 100 | 100 | 100 | 100 |
| MH-0060 | 5 | 100 | 100 | 100 | 100 |
| MH-0122 | 5 | 100 | 100 | 100 | 100 |
| MH-1889 | | 100 | 100 | 100 | 100 |
| MH-2653 | 15 | 100 | 100 | 100 | 100 |
| MH-2679 | 10 | 100 | 100 | 100 | 100 |
| MH-2781 | 5 | 100 | 100 | 100 | 100 |
| MH-2883 | 5 | 100 | 100 | 100 | 100 |
| MH-2895 | 5 | 100 | 100 | 100 | 100 |
| MH-2990 | 10 | 100 | 100 | 100 | 100 |
| MH-2998 | 5 | 100 | 100 | 100 | 100 |
| MH-4415 | 10 | 100 | 100 | 100 | 100 |
| MH-4418 | 10 | 100 | 100 | 100 | 100 |
| MH-5011 | 5 | 100 | 100 | 100 | 100 |
| MH-5017 | 10 | 100 | 100 | 100 | 100 |
| MH-5018 | 10 | 100 | 100 | 100 | 100 |
| MH-5511 | 10 | 100 | 100 | 100 | 100 |
| MH-9011 | 10 | 100 | 100 | 100 | 100 |

TABLE 10-2

Herbicidal Effects of Drechslera spp.- Acetanilide Chemical Herbicide Compositions

| Microorganism | — | E | F | G | H | I | J | K |
|---|---|---|---|---|---|---|---|---|
| — | 0 | 35 | 5 | 50 | 30 | 40 | 10 | 25 |
| MH-0015 | 5 | 100 | 90 | 100 | 100 | 100 | 85 | 100 |
| MH-0042 | 5 | 100 | 85 | 100 | 100 | 100 | 90 | 100 |
| MH-0060 | 5 | 100 | 85 | 100 | 100 | 100 | 85 | 100 |
| MH-0122 | 5 | 100 | 85 | 100 | 100 | 100 | 90 | 100 |
| MH-1889 | 5 | 100 | 90 | 100 | 100 | 100 | 95 | 100 |
| MH-2653 | 15 | 100 | 95 | 100 | 100 | 100 | 90 | 100 |
| MH-2679 | 10 | 100 | 90 | 100 | 100 | 100 | 85 | 100 |
| MH-2781 | 5 | 100 | 85 | 100 | 100 | 100 | 85 | 100 |
| MH-2883 | 5 | 100 | 85 | 100 | 100 | 100 | 85 | 100 |
| MH-2895 | 5 | 100 | 85 | 100 | 100 | 100 | 80 | 100 |
| MH-2990 | 10 | 100 | 90 | 100 | 100 | 100 | 90 | 100 |
| MH-2998 | 5 | 100 | 85 | 100 | 100 | 100 | 90 | 100 |
| MH-4415 | 10 | 100 | 100 | 100 | 100 | 100 | 100 | 100 |
| MH-4418 | 5 | 100 | 100 | 100 | 100 | 100 | 100 | 100 |
| MH-5011 | 5 | 100 | 100 | 100 | 100 | 100 | 100 | 100 |
| MH-5017 | 10 | 100 | 100 | 100 | 100 | 100 | 100 | 100 |
| MH-5018 | 10 | 100 | 100 | 100 | 100 | 100 | 100 | 100 |
| MH-5511 | 10 | 100 | 100 | 100 | 100 | 100 | 100 | 100 |
| MH-9011 | 10 | 100 | 100 | 100 | 100 | 100 | 100 | 100 |

TABLE 10-3

Herbicidal Effects of Drechslera spp.- Thiolcarbamate Chemical Herbicide Compositions

| Microorganism | — | L | M | N | O |
|---|---|---|---|---|---|
| — | 0 | 10 | 10 | 10 | 20 |
| MH-0015 | 10 | 90 | 95 | 85 | 90 |
| MH-0042 | 5 | 85 | 85 | 90 | 80 |
| MH-0060 | 5 | 85 | 80 | 90 | 90 |
| MH-0122 | 5 | 85 | 90 | 85 | 80 |
| MH-1889 | 5 | 95 | 90 | 90 | 95 |
| MH-2653 | 15 | 95 | 95 | 90 | 90 |

TABLE 10-3-continued

Herbicidal Effects of *Drechslera spp.*-
Thiolcarbamate Chemical Herbicide Compositions

| Microorganism | Chemical herbicide | | | | |
|---|---|---|---|---|---|
| | — | L | M | N | O |
| MH-2679 | 10 | 90 | 90 | 85 | 90 |
| MH-2781 | 5 | 85 | 80 | 90 | 90 |
| MH-2883 | 5 | 85 | 85 | 85 | 85 |
| MH-2895 | 5 | 85 | 90 | 85 | 90 |
| MH-2990 | 10 | 90 | 90 | 95 | 85 |
| MH-2998 | 5 | 85 | 85 | 80 | 85 |
| MH-4415 | 5 | 100 | 100 | 100 | 100 |
| MH-4418 | 10 | 100 | 100 | 100 | 100 |
| MH-5011 | 5 | 100 | 100 | 100 | 100 |
| MH-5017 | 10 | 100 | 100 | 100 | 100 |
| MH-5018 | 10 | 100 | 100 | 100 | 100 |
| MH-5511 | 10 | 100 | 100 | 100 | 100 |
| MH-9011 | 10 | 100 | 100 | 100 | 100 |

It is appreciated from Table 10-1 that, in the case of the compositions containing the Dreschslera strains according to the present invention in combination with the diphenyl ether herbicides, i.e., CNP, chlormethoxynil and bifenox or the diazine herbicide, i.e., oxadiazon, respectively, the herbicidal activities were synergistically enhanced compared with their single application.

It is understood from Table 10-2 that, in the case of the compositions containing the Drechslera strains according to the present invention in combination with the anilide herbicides, i.e., mefenacet, naproanilide, NSK-850, butachlor, pretilachlor, propanil and clomeprop, respectively, the herbicidal activities were synergistically enhanced compared with their single application.

It is envisaged from Table 10-3 that, in the case of the compositions containing the Drechslera strains according to the present invention in combination with the thiolcarbamate herbicides, i.e., benthiocarb, dimepiperate, molinate and esprocarb, respectively, the herbicidal activities were synergistically enhanced compared with their single application.

From the foregoing results, outstanding synergistic effects can be observed from compositions which contain Drechslera strains having pathogenecity against barnyard grass in combination with diphenyl ether herbicides, anilide herbicides, thiolcarbamate herbicides, diazine herbicides and like herbicides, said herbicides having all been employed as barnyard grass herbicides. Consequently, it has become possible to satisfactorily control barnyard grass by using such chemical herbicides even at a dosage as low as one tenth to one hundredth of their conventional dosage.

EXAMPLE 11

Herbicidal Effects of Weed Control Compositions, Which Contain Drechslera Strains and Chemical Herbicides in Combination, against Barnyard Grass - Flowable Formulations Barnyard grass seeds were planted in 1/1000-are pots contained in lowland soil, and the plants raising from the seeds were reared to the 1.5 leaf stage. The plants were irrigated to keep about 3 cm depth in water and treated with 1 μl (equivalent to one tenth of the standard dosage) of the flowable formulations prepared in the above formulation examples, respectively. The plants were then allowed to grow in a green house which was maintained at 35° C. during the day time and at 20° C. at night. Twenty days after the treatment, the remaining populations in the individual pots were counted. The control values against barnyard grass were calculated in accordance with the following formula and are shown in Tables ]1-1 to 11-3.

$$\text{Control value} = \frac{\text{Remaining population in untreated group} - \text{Remaining population in treated group}}{\text{Remaining population in untreated group}} \times 100$$

It is appreciated from Table 11-1 that, in the case of the compositions containing the Drechslera strains according to the present invention in combination with the diphenyl ether herbicide, i.e., CNP, respectively, the herbicidal activities were synergistically enhanced compared with their single application.

It is understood from Table 11-2 that, in the case of the compositions containing the Drechslera strains according to the present invention in combination with the anilide herbicides, i.e., mefenacet and pretilachlor, respectively, the herbicidal activities were synergistically enhanced compared with their single application.

It is envisaged from Table 11-3 that, in the case of the compositions containing the Drechslera strains according to the present invention in combination with the thiolcarbamate herbicides, i.e., benthiocarb and molinate, respectively, the herbicidal activities were synergistically enhanced compared with their single application.

TABLE 11-1

Herbicidal Effects of *Drechslera spp.*-CNP Compositions

| Microorganism | Chemical herbicide | |
|---|---|---|
| | — | CNP |
| — | 0 | 15 |
| MH-0015 | 5 | 100 |
| MH-0042 | 5 | 100 |
| MH-0060 | 5 | 100 |
| MH-0122 | 5 | 100 |
| MH-1889 | 10 | 100 |
| MH-2653 | 15 | 100 |
| MH-2679 | 10 | 100 |
| MH-2781 | 5 | 100 |
| MH-2883 | 5 | 100 |
| MH-2895 | 5 | 100 |
| MH-2990 | 10 | 100 |
| MH-2998 | 5 | 100 |
| MH-4415 | 5 | 100 |
| MH-4418 | 5 | 100 |
| MH-5011 | 10 | 100 |
| MH-5017 | 5 | 100 |
| MH-5018 | 10 | 100 |
| MH 5511 | 10 | 100 |
| MH-9011 | 10 | 100 |

TABLE 11-2

Herbicidal Effects of *Drechslera spp.*-Mefenacet/Pretilachlor Compositions

| Microorganism | Chemical herbicide | | |
|---|---|---|---|
| | — | Mefenacet | Pretilachlor |
| — | 0 | 25 | 30 |
| MH-0015 | 5 | 100 | 100 |
| MH-0042 | 5 | 100 | 100 |
| MH-0060 | 5 | 100 | 100 |
| MH-0122 | 5 | 100 | 100 |
| MH-1889 | 10 | 100 | 100 |
| MH-2653 | 15 | 100 | 100 |
| MH-2679 | 10 | 100 | 100 |
| MH-2781 | 5 | 100 | 100 |
| MH-2883 | 5 | 100 | 100 |
| MH-2895 | 5 | 100 | 100 |
| MH-2990 | 10 | 100 | 100 |

TABLE 11-2-continued

Herbicidal Effects of *Drechslera spp.*-Mefenacet/Pretilachlor Compositions

| Microorganism | Chemical herbicide | | |
|---|---|---|---|
| | — | Mefenacet | Pretilachlor |
| MH-2998 | 5 | 100 | 100 |
| MH-4415 | 5 | 100 | 100 |
| MH-4418 | 5 | 100 | 100 |
| MH-5011 | 10 | 100 | 100 |
| MH-5017 | 10 | 100 | 100 |
| MH-5018 | 10 | 100 | 100 |
| MH-5511 | 10 | 100 | 100 |
| MH-9011 | 10 | 100 | 100 |

TABLE 11-3

Herbicidal Effects of *Drechslera spp.*-Benthiocarb/Molinate Compositions

| Microorganism | Chemical herbicide | | |
|---|---|---|---|
| | — | Benthiocarb | Molinate |
| — | 0 | 15 | 10 |
| MH-0015 | 10 | 90 | 85 |
| MH-0042 | 5 | 80 | 80 |
| MH-0060 | 5 | 80 | 85 |
| MH-0122 | 5 | 85 | 85 |
| MH-1889 | 5 | 95 | 95 |
| MH-2653 | 15 | 90 | 95 |
| MH-2679 | 10 | 95 | 90 |
| MH-2781 | 5 | 80 | 80 |
| MH-2883 | 5 | 85 | 85 |
| MH-2895 | 5 | 85 | 80 |
| MH-2990 | 10 | 95 | 90 |
| MH-2998 | 5 | 80 | 85 |
| MH-4415 | 5 | 100 | 100 |
| MH-4418 | 5 | 100 | 100 |
| MH-5011 | 10 | 100 | 100 |
| MH-5017 | 10 | 100 | 100 |
| MH-5018 | 10 | 100 | 100 |
| MH-5511 | 10 | 100 | 100 |
| MH-9011 | 10 | 100 | 100 |

EXAMPLE 12

Herbicidal Effects of Weed Control Compositions, Which Contain Drechslera Strains and Chemical Herbicides in Combination, against Barnyard Grass - Flowable Formulations Barnyard grass seeds were planted in 1/1000-are pots contained in lowland soil, and the plants raising from the seeds were reared to the 1.5 leaf stage. The plants were irrigated to keep about 3 cm depth in water and treated with 1.5 µl (equivalent to one tenth of the standard dosage) of the flowable formulations prepared in the above formulation examples, respectively. The plants were then allowed to grow in a green house which was maintained at 35° C. during the day time and at 20° C. at night. Twenty days after the treatment, the remaining populations in the individual pots were counted. The control valves against barnyard grass were calculated in accordance with the following formula and are shown in Table 12.

$$\text{Control value} = \frac{\text{Remaining population in untreated group} - \text{Remaining population in treated group}}{\text{Remaining population in untreated group}} \times 100$$

In the table, A, E, I and L represent the following herbicides.
A: CNP
E: Mefenacet
I: Pretilachlor
L: Benthiocarb It is appreciated from Table 12 that, in the case of the compositions containing the Drechslera strains according to the present invention in combination with the diphenyl ether herbicide, i.e., CNP, respectively, the herbicidal activities were synergistically enhanced compared with their single application.

It is understood from Table 12 that, in the case of the compositions containing the Drechslera strains according to the present invention in combination with the anilide herbicides, i.e., mefenacet and pretilachlor, respectively, the herbicidal activities were synergistically enhanced compared with their single application.

It is envisaged from Table 12 that, in the case of the compositions containing the Drechslera strains according to the present invention in combination with the thiol carbamate herbicides, i.e., benthiocarb and molinate, respectively, the herbicidal activities were synergistically enhanced compared with their single application.

TABLE 12

Herbicidal Effects of *Drechslera spp.*-Chemical Herbicide Compositions

| Microorganism | Chemical herbicide | | | | |
|---|---|---|---|---|---|
| | — | A | E | I | L |
| — | 0 | 10 | 20 | 30 | 10 |
| MH-0015 | 10 | 90 | 90 | 90 | 90 |
| MH-0042 | 5 | 85 | 85 | 85 | 85 |
| MH-0060 | 5 | 85 | 85 | 85 | 85 |
| MH-0122 | 5 | 85 | 85 | 85 | 85 |
| MH-1889 | 5 | 95 | 95 | 100 | 95 |
| MH-2653 | 15 | 95 | 95 | 95 | 95 |
| MH-2679 | 10 | 90 | 90 | 90 | 90 |
| MH-2781 | 5 | 85 | 85 | 85 | 85 |
| MH-2883 | 5 | 85 | 85 | 85 | 85 |
| MH-2895 | 5 | 85 | 85 | 85 | 85 |
| MH-2990 | 10 | 90 | 90 | 90 | 90 |
| MH-2998 | 5 | 85 | 85 | 85 | 85 |
| MH-4415 | 5 | 100 | 100 | 100 | 100 |
| MH-4418 | 5 | 100 | 100 | 100 | 100 |
| MH-5011 | 10 | 100 | 100 | 100 | 100 |
| MH-5017 | 10 | 100 | 100 | 100 | 100 |
| MH-5018 | 10 | 100 | 100 | 100 | 100 |
| MH-5511 | 10 | 100 | 100 | 100 | 100 |
| MH-9011 | 10 | 100 | 100 | 100 | 100 |

EXAMPLE 13

Herbicidal Effects of Weed Control Compositions, which contained Drechslera Strains and Chemical Herbicides in combination, against Barnyard grass and Broadleaf weeds Barnyard grass, monochoria (Monochoria vaginalis) and narrowleaf waterplantain were separately seeded in lowland soil which was contained in 1/1000-are pots, and were reared to the 1.5 leaf stage. The pots which were in a state irrigated to about 3 cm in water depth were treated with 1.5 mg (equivalent to one tenth of the standard dosage) of the various compositions prepared above in Formulation Examples 1-33, respectively. The seedlings were then allowed to grow in a green house which was maintained at 35° C. during the day time and at 20° C. at night. Twenty days after the treatment, the remaining populations in the individual pots were counted. The control values against barnyard grass, monochoria or narrowleaf waterplantain were calculated in accordance with the following formula and are shown in Tables 13 - 1 to 13-3.

$$\text{Control value} = \frac{\text{Remaining population in untreated group} - \text{Remaining population in treated group}}{\text{Remaining population in untreated group}} \times 100$$

In the tables, P-S represent the following herbicides.
A: CNP
P: Bensul furon methyl
Q: Pyrazosul fron ethyl
R: Pyrazolate
S: Simetryne

TABLE 13-1

Herbicidal Effects of *Drechslera spp.*-Chemical Herbicide Compositions against Barnyard Grass

| Microorganism | Chemical herbicide | | | | |
|---|---|---|---|---|---|
| | — | P | Q | R | S |
| — | 0 | 10 | 20 | 30 | 10 |
| MH-0015 | 10 | 90 | 90 | 90 | 90 |
| MH-0042 | 5 | 85 | 85 | 85 | 85 |
| MH-0060 | 5 | 85 | 85 | 85 | 85 |
| MH-0122 | 5 | 85 | 85 | 85 | 85 |
| MH-1889 | 5 | 95 | 90 | 100 | 85 |
| MH-2653 | 15 | 95 | 95 | 95 | 95 |
| MH-2679 | 10 | 90 | 90 | 90 | 90 |
| MH-2781 | 5 | 85 | 85 | 85 | 85 |
| MH-2883 | 5 | 85 | 85 | 85 | 85 |
| MH-2895 | 5 | 85 | 85 | 85 | 85 |
| MH-2990 | 10 | 90 | 90 | 90 | 90 |
| MH-2998 | 5 | 85 | 85 | 85 | 85 |
| MH-4415 | 5 | 100 | 100 | 100 | 100 |
| MH-4418 | 5 | 100 | 100 | 100 | 100 |
| MH-5011 | 10 | 100 | 100 | 100 | 100 |
| MH-5017 | 10 | 100 | 100 | 100 | 100 |
| MH-5018 | 10 | 100 | 100 | 100 | 100 |
| MH-5511 | 10 | 100 | 100 | 100 | 100 |
| MH-9011 | 10 | 100 | 100 | 100 | 100 |

TABLE 13-2

Herbicidal Effects of *Drechslera spp.*-Chemical Herbicide Compositions against Monochoria

| Microorganism | Chemical herbicide | | | | |
|---|---|---|---|---|---|
| | — | P | Q | R | S |
| — | 0 | 90 | 90 | 80 | 80 |
| MH-0015 | 0 | 90 | 90 | 90 | 90 |
| MH-0042 | 0 | 85 | 85 | 85 | 85 |
| MH-0060 | 0 | 85 | 85 | 85 | 85 |
| MH-0122 | 0 | 85 | 85 | 85 | 85 |
| MH-1889 | 0 | 90 | 95 | 90 | 90 |
| MH-2653 | 0 | 95 | 95 | 95 | 95 |
| MH-2679 | 0 | 90 | 90 | 90 | 90 |
| MH-2781 | 0 | 85 | 85 | 85 | 85 |
| MH-2883 | 0 | 85 | 85 | 85 | 85 |
| MH-2895 | 0 | 85 | 85 | 85 | 85 |
| MH-2990 | 0 | 90 | 90 | 90 | 90 |
| MH-2998 | 0 | 85 | 85 | 85 | 85 |
| MH-4415 | 0 | 100 | 100 | 100 | 100 |
| MH-4418 | 0 | 100 | 100 | 100 | 100 |
| MH-5011 | 0 | 100 | 100 | 100 | 100 |
| MH-5017 | 0 | 100 | 100 | 100 | 100 |
| MH-5018 | 0 | 100 | 100 | 100 | 100 |
| MH-5511 | 0 | 100 | 100 | 100 | 100 |
| MH-9011 | 0 | 100 | 100 | 100 | 100 |

TABLE 13-3

Herbicidal Effects of *Drechslera spp.*-Chemical Herbicide Compositions Against Narrowleaf Waterplantain

| Microorganism | Chemical herbicide | | | | |
|---|---|---|---|---|---|
| | — | P | Q | R | S |
| — | 0 | 85 | 85 | 80 | 90 |
| MH-0015 | 0 | 90 | 90 | 90 | 90 |
| MH-0042 | 0 | 85 | 85 | 85 | 85 |
| MH-0060 | 0 | 85 | 85 | 85 | 85 |
| MH-0122 | 0 | 85 | 85 | 85 | 85 |
| MH-1889 | 0 | 95 | 95 | 100 | 95 |
| MH-2653 | 0 | 95 | 95 | 95 | 95 |
| MH-2679 | 0 | 90 | 90 | 90 | 90 |
| MH-2781 | 0 | 85 | 85 | 85 | 85 |
| MH-2883 | 0 | 85 | 85 | 85 | 85 |
| MH-2895 | 0 | 85 | 85 | 85 | 85 |
| MH-2990 | 0 | 90 | 90 | 90 | 90 |
| MH-2998 | 0 | 85 | 85 | 85 | 85 |
| MH-4415 | 0 | 100 | 100 | 100 | 100 |
| MH-4418 | 0 | 100 | 100 | 100 | 100 |
| MH-5011 | 0 | 100 | 100 | 100 | 100 |
| MH-5017 | 0 | 100 | 100 | 100 | 100 |
| MH-5018 | 0 | 100 | 100 | 100 | 100 |
| MH-5511 | 0 | 100 | 100 | 100 | 100 |
| MH-9011 | 0 | 100 | 100 | 100 | 100 |

It is appreciated from Table 13-1 that, in the case of the compositions containing the Drechslera strains according to the present invention in combination with the sulfonylurea herbicides, i.e., bensulfuron methyl and pyrazosulfron ethyl, the. diazine herbicide, i.e., pyrazolate or the triazine herbicide, i.e., simetryne, respectively, the herbicidal activities against barnyard grass were synergistically enhanced compared with their single application.

It is understood from Tables 13-2 and 13-3 that, in the case of the compositions containing the Drechslera strains according to the present invention in combination with the sulfonylurea herbicides, i.e., bensulfuron methyl and pyrazosulfron ethyl, the diazine herbicide, i.e., pyrazolate or the triazine herbicide, i.e., simetryne, respectively, the herbicidal activities against the broadleaf weeds, namely, monochoria or narrowleaf waterplantain were enhanced to some extent compared with their single application.

It is also envisaged from Table 13-1 that, in the case of the compositions containing the Drechslera strains according to the present invention in combination with the sulfonylurea herbicides, i.e., bensulfuron methyl and pyrazosulfron ethyl, the diazine herbicide, i.e., pyrazolate or the triazine herbicide, i.e., simetryne, respectively, sufficient weed control effects were also exhibited against the broadleaf weeds, namely, monochoria or narrowleaf waterplantain compared with their single application and increased practical utility was observed.

From the foregoing results, it is understood that compositions containing Drechslera strains having pathogenecity against barnyard grass in combination with sulfonylurea herbicides such as bensulfuron methyl and pyrazosulfron ethyl, diazine herbicides such as pyrazolate or triazine herbicides such as simetryne - said herbicides having been employed against broadleaf weeds - can exhibit enhanced weed control effects against barnyard grass and also a broadened spectrum and enhanced herbicidal effects against broadleaf weeds although the enhancement of their herbicidal effects against broadleaf weeds is not substantial. These compositions are therefore believed to have practical utility.

The combined use with broadleaf weed herbicides makes it possible to reduce the dosage of conidia of each strain of Drechslera spp.. This in turn makes it possible to reduce the production cost.

EXAMPLE 14

Dosage Reduction of Conidia by Synergistic Effects of Drechslera Strains and Chemical Herbicides Barnyard grass seeds were planted in 1/1000-are pots contained in lowland soil, and the plants raising from the seeds were reared to the 1.5 leaf stage. The plants were irrigated to keep about 3 cm depth in water and treated with predetermined amounts of conidia and also with a prescribed amount (equivalent to one tenth of the standard dosage) of the broadleaf weed herbicide, bensulfuron. The plants were then allowed to grow in a green house which was maintained at 35° C. during the day time and at 20° C. at night. Twenty days after the treatment, the remaining populations in the individual pots were counted. The control values against barnyard grass were calculated in accordance with the following formula and are shown in Table 14.

$$\text{Control value} = \frac{\begin{array}{c}\text{Remaining population in} \\ \text{untreated group}\end{array} - \begin{array}{c}\text{Remaining population in} \\ \text{treated group}\end{array}}{\text{Remaining population in untreated group}} \times 100$$

TABLE 14

Reduction in Conidium Dosage owing to Synergistic Effects of *Drechslera* Strains and Chemical Herbicide

| Micoorganism MH-5511 | Microorganism alone | Bensulfuron + Microorganism |
|---|---|---|
| $1 \times 10^6$ | 100 | 100 |
| $3 \times 10^5$ | 80 | 100 |
| $1 \times 10^5$ | 50 | 100 |
| $3 \times 10^4$ | 30 | 70 |
| $1 \times 10^4$ | 10 | 50 |
| 0 | 0 | 10 |
| | (Untreated) | (Herbicide alone) |

List of Deposited Microorganisms (International Deposit under the Budapest Treaty)

| Name of Strain | Date of Deposit | Deposit No. |
|---|---|---|
| MH-0015 | June 17, 1989 | FERM BP-2652 |
| MH-0042 | October 28, 1988 | FERM BP-2659 |
| MH-0060 | September 28, 1989 | FERM BP-2657 |
| MH-0122 | August 31, 1989 | FERM BP-2655 |
| MH-1889 | February 7, 1991 | FERM BP-3410 |
| MH-2653 | June 17, 1989 | FERM BP-2653 |
| MH-2679 | August 31, 1989 | FERM BP-2656 |
| MH-2781 | June 8, 1990 | FERM BP-3407 |
| MH-2883 | June 8, 1990 | FERM BP-3408 |
| MH-2895 | June 8, 1990 | FERM BP-3409 |
| MH-4415 | February 22, 1991 | FERM BP-3413 |
| MH-4418 | February 22, 1991 | FERM BP-3414 |
| MH-5011 | February 22, 1991 | FERM BP-3415 |
| MH-5017 | February 7, 1991 | FERM BP-3411 |
| MH-5018 | February 7, 1991 | FERM BP-3412 |
| MH-5511 | March 27, 1991 | FERM BP-3417 |
| MH-9011 | March 27, 1991 | FERM BP-3416 |

What is claimed is:

1. A method of controlling a wild type barnyard grass selected from the group consisting of *Echinochloa-crus-*galli var. crus-galli, *Echinochloa-crus-*galli var. formosensis, *Echinochloa-crus-*galli var. praticola, *Echinochloa oryzicola* and *Echinochloa colonum,* which method comprises applying to the locus of the wild type barnyard grass to control the growth of the wild type barnyard grass an effective growth controlling amount of at least one strain selected from the group consisting of *Drechslera monoceras* FERM BP-2652, FERM BP-3410, FERM BP-2653, FERM BP-2656, FERM BP-3413, FERM BP-3414, FERM BP-3415, FERM BP-3411, FERM BP-3412, FERM BP-3417 and FERM BP-3416, *Drechslera ravenelli* FERM BP-2659, FERM BP-2657 and FERM BP-3408, and *Drechslera poae* FERM BP-2655, FERM BP-3407 and FERM BP-3409.

2. A composition for controlling wild type barnyard grass selected from the group consisting of *Echinochloa-crus-*galli var. crus-galli, *Echinochloa-crus-*galli var. formosenis, *Echinochloa-crus-*galli var. praticola, *Echinochloa oryzicola* and *Echinochloa colonum,* said composition comprising:

(a) an agriculturally acceptable carrier, and (b) an effective growth-controlling amount of one or more strains selected from the group consisting of *Drechslera monoceras* FERM BP-2652, FERM BP-3410, FERM BP-2653, FERM BP-2656, FERM BP-3413, FERM BP-3414, FERM BP-3415, FERM BP-3411, FERM BP-3412, FERM BP-3417 and FERM BP-3416, *Drechslera ravenelli* FERM BP-2659, FERM BP-2657 and FERM BP-3408, and *Drechslera poae* FERM BP-2655, FERM BP-3407 and FERM BP-3409.

3. The composition of claim 2, which contains one or more of said strains in an amount of $10^2$ to $10^{12}$ spores per kilogram of composition.

4. A biologically pure culture of the genus Drechslera selected from the group consisting of *Drechslera monoceras* FERM BP-2652, FERM BP-3410, FERM BP-2653, FERM BP-2656, FERM BP-3413, FERM BP-3414, FERM BP-3415, FERM BP-3411, FERM BP-3412, FERM BP-3417 and FERM BP-3416, *Drechslera ravenelli* FERM BP-2659, FERM BP-2657 and FERM BP-3408, and *Drechslera poae* FERM BP-2655, FERM BP-3407 and FERM BP-3409.

* * * * *